United States Patent
Lee et al.

(10) Patent No.: US 12,275,999 B2
(45) Date of Patent: *Apr. 15, 2025

(54) POLYNUCLEOTIDES FOR THE AMPLIFICATION AND DETECTION OF CHLAMYDIA TRACHOMATIS

(71) Applicant: Talis Biomedical Corporation, Menlo Park, CA (US)

(72) Inventors: Matthew B. Lee, San Jose, CA (US); Hedia Maamar, San Jose, CA (US)

(73) Assignee: Talis Biomedical Corporation, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/349,185

(22) PCT Filed: Nov. 13, 2017

(86) PCT No.: PCT/US2017/061402
§ 371 (c)(1),
(2) Date: May 10, 2019

(87) PCT Pub. No.: WO2018/089942
PCT Pub. Date: May 17, 2018

(65) Prior Publication Data
US 2019/0284617 A1   Sep. 19, 2019

Related U.S. Application Data

(60) Provisional application No. 62/420,488, filed on Nov. 10, 2016.

(51) Int. Cl.
| | | |
|---|---|---|
| C12Q 1/68 | (2018.01) | |
| C07H 21/00 | (2006.01) | |
| C07H 21/04 | (2006.01) | |
| C12Q 1/6844 | (2018.01) | |
| C12Q 1/689 | (2018.01) | |

(52) U.S. Cl.
CPC .............. *C12Q 1/689* (2013.01); *C07H 21/00* (2013.01); *C07H 21/04* (2013.01); *C12Q 1/6844* (2013.01)

(58) Field of Classification Search
None
See application file for complete search history.

(56) References Cited

U.S. PATENT DOCUMENTS

| | | |
|---|---|---|
| 5,155,018 A | 10/1992 | Gillespie et al. |
| 5,173,401 A | 12/1992 | Wolff et al. |
| 5,234,809 A | 8/1993 | Boom et al. |
| 5,389,515 A | 2/1995 | Chmelo et al. |
| 5,512,445 A | 4/1996 | Yang et al. |
| 5,804,141 A | 9/1998 | Chianese |
| 5,830,643 A | 11/1998 | Yamamoto et al. |
| 6,001,611 A | 12/1999 | Will |
| 6,383,393 B1 | 5/2002 | Colpan et al. |
| 7,504,111 B2 | 3/2009 | Fontana et al. |
| 7,728,119 B2 | 6/2010 | Nakamura et al. |
| 7,897,744 B2 | 3/2011 | Plummer et al. |
| 8,993,718 B2 | 3/2015 | Gross et al. |
| 9,187,789 B2 | 11/2015 | Pabich et al. |
| 9,434,999 B1 | 9/2016 | Ao et al. |
| 9,982,312 B2 | 5/2018 | Pearce et al. |
| 9,994,916 B2 | 6/2018 | Thornton et al. |
| 10,252,264 B2 | 4/2019 | Shen et al. |
| 10,450,616 B1 | 10/2019 | Dedent et al. |
| 10,500,267 B2 | 12/2019 | LeFebvre et al. |
| 10,907,222 B2 | 2/2021 | Jeon et al. |
| 10,954,572 B2 | 3/2021 | Dedent et al. |
| 11,047,007 B1 | 6/2021 | Andini et al. |
| 11,326,214 B2 | 5/2022 | Dedent et al. |
| 2004/0091870 A1 | 5/2004 | Pabich et al. |
| 2004/0132218 A1 | 7/2004 | Ho |
| 2006/0216212 A1 | 9/2006 | Lum et al. |
| 2006/0257874 A1* | 11/2006 | Tisi ..................... C12Q 1/6851 435/6.14 |
| 2007/0061898 A1 | 3/2007 | Yang et al. |
| 2007/0087336 A1 | 4/2007 | Sampath et al. |
| 2007/0161590 A1 | 7/2007 | Van Bilsen et al. |
| 2007/0202523 A1* | 8/2007 | Becker .................... C12P 19/34 435/6.12 |
| 2008/0152587 A1 | 6/2008 | Zhou et al. |
| 2008/0276335 A1 | 11/2008 | Abad et al. |
| 2008/0299567 A1 | 12/2008 | Marshall et al. |

(Continued)

FOREIGN PATENT DOCUMENTS

| | | |
|---|---|---|
| CN | 1592792 A | 3/2005 |
| CN | 101305101 A | 11/2008 |
| CN | 101831488 A | 9/2010 |
| CN | 101886122 A | 11/2010 |
| CN | 102559861 A | 7/2012 |
| CN | 102918155 A | 2/2013 |
| CN | 107099618 A | 8/2017 |
| JP | 2012060940 A | 3/2012 |
| JP | 2012130290 A | 7/2012 |
| JP | 5710190 B2 | 4/2015 |
| JP | 2017038572 A | 2/2017 |
| KR | 101742016 B1 | 5/2017 |

(Continued)

OTHER PUBLICATIONS

Choopara et al. Development of chlamydia trachomatis detection by loop-mediated isothermal amplification. International journal of Biomedical sciences and Bioinformatics, vol. 2(1), pp. 21-25, (2015).*

(Continued)

*Primary Examiner* — Suryaprabha Chunduru
(74) *Attorney, Agent, or Firm* — Shay Glenn LLP

(57) ABSTRACT

The invention provides methods and compositions for the detection of *Chlamydia trachomatis* in a test sample. Its presence or absence in the sample is determined by nucleic acid based testing methods using primers and/or probes and or molecular beacons that bind to the 16S or 23S ribosomal genes or gene transcripts.

11 Claims, No Drawings
Specification includes a Sequence Listing.

(56) References Cited

U.S. PATENT DOCUMENTS

| | | |
|---|---|---|
| 2008/0318282 A1 | 12/2008 | Uematsu et al. |
| 2009/0130656 A1 | 5/2009 | Whiley et al. |
| 2009/0226885 A1 | 9/2009 | Sillekens et al. |
| 2009/0253622 A1 | 10/2009 | Van Noort et al. |
| 2010/0021886 A1 | 1/2010 | Wang et al. |
| 2010/0267012 A1 | 10/2010 | Bergeron et al. |
| 2012/0052503 A1 | 3/2012 | Li |
| 2012/0100551 A1 | 4/2012 | Kojima et al. |
| 2013/0017539 A1 | 1/2013 | Singhal et al. |
| 2013/0039938 A1 | 2/2013 | Smith et al. |
| 2013/0265054 A1 | 10/2013 | Lowery et al. |
| 2013/0323738 A1 | 12/2013 | Tanner et al. |
| 2014/0072971 A1 | 3/2014 | Wuitschick et al. |
| 2014/0308663 A1 | 10/2014 | Yonekawa et al. |
| 2014/0349295 A1 | 11/2014 | Hosaka et al. |
| 2015/0159205 A1 | 6/2015 | Narayanan et al. |
| 2015/0267266 A1 | 9/2015 | Soetaert et al. |
| 2015/0322493 A1 | 11/2015 | Tulp et al. |
| 2016/0024562 A1 | 1/2016 | Pabich et al. |
| 2016/0076083 A1 | 3/2016 | Ellington et al. |
| 2016/0257998 A1 | 9/2016 | Persing et al. |
| 2016/0273029 A1 | 9/2016 | Suwara et al. |
| 2016/0289730 A1 | 10/2016 | Pezacki et al. |
| 2016/0319378 A1 | 11/2016 | Rey |
| 2017/0260572 A1 | 9/2017 | Filer et al. |
| 2017/0283884 A1 | 10/2017 | Knudsen |
| 2019/0111423 A1 | 4/2019 | Ismagilov et al. |
| 2019/0284618 A1 | 9/2019 | Dedent et al. |
| 2021/0164043 A1 | 6/2021 | Casolan et al. |
| 2021/0254139 A1 | 8/2021 | Dedent et al. |
| 2021/0292854 A1 | 9/2021 | Andini et al. |
| 2021/0340622 A1 | 11/2021 | Andini et al. |
| 2022/0251630 A1 | 8/2022 | Dedent et al. |

FOREIGN PATENT DOCUMENTS

| | | | | |
|---|---|---|---|---|
| WO | WO2002/079243 A2 | 10/2002 | | |
| WO | WO2006/133385 A2 | 12/2006 | | |
| WO | WO2007/096184 A1 | 8/2007 | | |
| WO | WO2009/099037 A1 | 8/2009 | | |
| WO | WO2010/010951 A1 | 1/2010 | | |
| WO | WO2011/004397 A1 | 1/2011 | | |
| WO | WO2011/091330 A1 | 7/2011 | | |
| WO | WO2011/144304 A1 | 11/2011 | | |
| WO | WO2012/021802 A2 | 2/2012 | | |
| WO | WO2012/032489 A1 | 3/2012 | | |
| WO | WO2013/132452 A2 | 9/2013 | | |
| WO | WO-2014060604 A2 * | 4/2014 | ............ | A61B 18/22 |
| WO | WO2015/058008 A2 | 4/2015 | | |
| WO | WO2015/147415 A1 | 10/2015 | | |
| WO | WO2016/011280 A1 | 1/2016 | | |
| WO | WO2016/085632 A2 | 6/2016 | | |
| WO | WO-2016105508 A2 * | 6/2016 | ........ | B01L 3/502723 |
| WO | WO2017/103269 A1 | 6/2017 | | |
| WO | WO2017/192902 A1 | 11/2017 | | |
| WO | WO2018/031531 A1 | 2/2018 | | |

OTHER PUBLICATIONS

Jevtuševskaja, J. et al., "Combination with antimicrobial peptide lyses improves loop-mediated isothermal amplification based method for *Chlamydia trachomatis* detection directly in urine sample," BMC Infectious Diseases, (2016) 16:329.

Liu, M., et al., "Loop-mediated isothermal amplification of *Neisseria gonorrhoeae* porA pseudogene: a rapid and reliable method to detect gonorrhea," AMB Express, (2017) 7:48.

Falk et al.; Sampling for Chlamydia trachomatis infection comparison of vaginal, first-catch urine, combined vaginal and first-catch urine and endocervical sampling; International journal of STD & AIDS; 21(4); pp. 283-287; Apr. 2010.

Michel et al.; Chlamydia trachomatis load at matched anatomic sites: implications for screening strategies; Journal of clinical microbiology; 45(5); pp. 1395-1402; May 2007.

Notomi et al.; Loop-mediated isothermal amplification of DNA; Nucleic acids research; 28(12); e63; Jun. 15, 2000.

Papp et al.; Recommendations for the laboratory-based detection of Chlamydia trachomatis and Neisseria gonorrhoeae—2014; MMWR; Recommendations and reports: Morbidity and mortality weekly report. Recommendations and reports/Centers for Disease Control; 63(1): 19 pages; Mar. 3, 2014.

Priest et al.; Neisseria gonorrhoeae DNA bacterial load in men with symptomatic and asymptomatic gonococcal urethritis; Sexually Transmitted Infections ;93(7); pp. 478-481; Nov. 1, 2017.

Dedent et al.; U.S. Appl. No. 18/296,978 entitled "Polynucleotides for the amplification and detection of neisseria gonorrhoeae," filed Apr. 6, 2023.

Chui et al.; A comparison of three real-time PCR assays for the confirmation of Neisseria gonorrhoeae following detection of N. gonorrhoeae using Roche COBAS AMPLICOR. Clinical microbiology and infection; 14(5); pp. 473-479; May 1, 2008.

Kubota et al.; FRET-based assimilating probe for sequence-specific real-time monitoring of loop-mediated isothermal amplification (LAMP); Biological Engineering Transactions; 4(2); pp. 81-100; Jan. 2011.

Bakheit et al.; Sensitive and specific detection of crptosporidium species in PCR-negative samples by loop-mediated isothermal DNA amplification and confirmation of generated LAMP products by sequencing; Veterinary Paraitology; 158(1-2); pp. 11-22; Nov. 2008.

Beaucage et al.; Deoxynucleoside phosphoramidites—a new class of key intermediates for deoxypolynucleotide synthesis; Tetrahedron Letters; 22(20); pp. 1859-1862; Jan. 1981.

Broude; Stem-loop obligonucleotides: a robust tool for molecular biology and biotechnology; Trends in biotechnology; 20(6); pp. 249-256; Jun. 2002.

Cady; Quantum dot molecular beacons for DNA detection; Micro and Nano Technologies in Bioanalysis; 554; pp. 367-379; 2009 (the year of publication is sufficiently earlier than the effective U.S. filing date and any foreign priority date so that the particular month of publication is not in issue.

Choopara et al.; Development of chlamydia trachomatis detection by loop-mediated isothermal amplification; International Journal of Biomedical Sciences and Bioformatics; 2(1); pp. 21-25; 2015 (the year of publication is sufficiently earlier than the effective U.S. filing date and any foreign priority date so that the particular month of publication is not in issue).

Choopara et al.; Rapid and visual chalmydia trachomatis detection using loop-mediated isothermal amplification and hydroxynaphthol blue; Letters in Applied Microbiology; 64(1); pp. 51-56; Sep. 2016.

Cissell et al.; Resonance energy transfer methods of RNA detection; Analytical and Bioanalytical Chenistry; 393(1); pp. 125-135; Jan. 2009.

Edwards et al.; Loop-mediated isothermal amplification test for detection of neisseria gonorrhoease in urine samples and tolerance of the assay to the presence of urea; Journal of Clinical Microbiology; 52(6); pp. 2163-2165; Jun. 2014.

Eiken Chemical Co .; A guide to LAMP primer designing, PrimerExplorer V4; 19 pages; retrieved from the internet(https://primerexplorer.jp/e/v4_manual/pdf/PrimerExplorerV4_Manual_1.pdf) on Oct. 20, 2022.

Fan et al.; The Development and evaluation of a loop-mediated isothermal amplification method for the rapid detection of salmonella enterica serovar typhi; Plos One; 10(4); eo124507; 13 pages; Apr. 2015.

Gandelman et al.; Loop-mediated amplification accelerated by stem primers; International Journal of Molecular Sciences; pp. 9108-9124; Dec. 2011.

GenBank Acession No. X67293, N. gonorrhoeae gene for 23S rRNA, 2pages; retrieved from the internet (https: nobi.nlm.nih.gov/nucleotide/X67293.1?report=genobank&log$=nuclalign&blast_rank=95&RID=XZXX9U6R016) on Jan. 13, 2022.

GENBANK submission AC127341.3; Mus musculus BAC clone RP23-189L19 from chromosome 17, complete sequence; Nov. 23, 2003 [Online]: 2 pages; retrieved from the internet (https://www.nvbi.nlm.gov/nuccore/AC127341) on Jul. 29, 2021.

(56) References Cited

OTHER PUBLICATIONS

GENBANK submission AE004969.1, Neisseria gonorrhoeae FA 1090 complete genome, 2 pages; Jul. 1, 2015 [online]; retrieved from the internet (https://www.ncbi.nlm.nih.gov/nuccore/AE004969) on Nov. 23, 2020.
GENBANK submission AFY24545.1; glycoprotien 5 (Porcine reproductive and respiratory syndrome virus; Feb. 28, 2013 [online]; 2 pages; retrieved from the internet (https://www.ncbi.nim.gov/prtein/AFY24545) on Jul. 29, 2021.
GENBANK submission AL16244.1; Tetraodon nigrovirdis genome survey sequence PC-Ori end clone 198J04 of library G from Tetraodon nigroviridis, genomic survey sequence, Sep. 1, 2000 [online] 2 pages; retrieved from the internet (https://www.ncbi.nlm.nih.gov/nuccore/AL169244) on Jul. 29, 2021.
GENBANK submission CP019169.1; Betaproteobacteria bacterium GR16-43 chromosome, complete genome; Jan. 17, 2017 [online]; 2 pages; retrieved from the internet (https://www.nobi.nim.nih.gov/nuccore/CP019169) on Jul. 29, 2021.
GENBANK submission CZ791141.1, OC_Ba0158F23.fOC_BaOryza coarctata genomic clone OC_Ba158F23 5", genomic survey sequence; Aug. 29, 2012 [online]; 2 pages; retrieved from the internet (https://www.ncbi.nim.nih.gov/nuccore/CZ791141.1) on Jul. 29, 2021.
GENBANK submission EK565433.1, 1095521038908 Global-Ocen-Sampling_GS-32-01-01-1P3-1P6KB marine metagenome genomic clone 1061005966854 5' genomic survey sequence, 2 pages; May 26, 2010 [online]; retrieved from the internet (https://www.ncbi.nim.nih.gov/nuccore/EK565433 on Nov. 23, 2020.
GENBANK submission HS475166.1, BL-57332 Nilaparvata lugens illumina library Nilaparvata luens cDNA 5', mRNA sequence, May 3, 2011 [online]; 1 page; retienved from the internet (https://www.nobi.nim.nih.gov/nuccore/HS475166) on Jul. 29, 2021.
GENBANK submission LR606187.1; Aquila chrysaetos chrysaetos genome assembly, chromosome; Jul. 4, 2019 [online] 1 pag; retrieved from the internet (https:/www.ncbi.nih.gov/nuccore/LR606187) on Nov. 23, 2020.
GENBANK submission LS483369.1, Neisseria cinerea strain NCTC10294 genome assembly, chromosome: 1, Jun. 17, 2018 [online]; 1 page; retrieved from the internet (https://www.nobi.nim.nih.gov/nuccore/L.$483369) on Nov. 23, 2020.
Iwamoto et al.; Loop-mediated isothermal amplification for direct detection of mycobacterium tuberculosis complex m. avium, and m. intracellulare in sputum samples; Journal of clinical Microbology; 41(6); pp. 2616-2622; Jun. 2003.
Jepsen et al.; Locked nucleic acid: potent nucleic acid analog in therapeutics and biotechnology: Oligonucleotides; 14(2); pp. 130-146; 2004 (the year of publication is sufficiently earlier than the effective U.S. filing date and any foreign priority date so that the particular month of publication is not in issue).
Johns Hopkins Univeristy; Coronavirus resource center; 1 page; retrieved from the internet (https://coronavirus.jhu.edu/map.html) on Oct. 14, 2022.
Juskowiak; Nucleic acid-based flourescent probes and their analytical potential; Analytical and Bioanalytical Chemistry; 399(9); pp. 3157-3176; Mar. 2011.
Katoh et al.; MAFFT multiple sequence alignment software version 7: improvements in performance and useability; Molecular Biology and Evolution; 30(4); pp. 772-780; Apr. 2013.
Lee et al.; Clinical evaluation of a loop-mediated isothermal amplification (LAMP) assay for rapid detection of neisseria meningitidis in cerebrospinal fluid; Plos One; 10(4); e0122922; 13 pages; Apr. 2015.
Li et al.; Molecular beacons: an optimal multifunctional biological probe; Biochemical and Biophysical Research Communications; 373(4); pp. 457-461; Sep. 2008.
Little et al.; Strand displacement amplification and homogeneous real-time detection incorporated in a second-generation dna probe system, BDProbe TecET; Clinical Chemistry; 45(6); pp. 777-784; Jun. 1999.
Liu et al.; Establishment of an accurate and fast detection method using molecular beacons in loop-mediated isothermal amplification assay; Scientific reports; 7(1); pp. 1-9; doi:10.1038/srep40125; Janaury 2017.
Lowe et al.; A computer program for selection of olignucleotide primers for polymerase chain reactions; Nucleic Acids Research; 18(7); pp. 1757-1761; Apr. 1990.
Nagamine et al.; Accelerated reaction by loop-mediated isothermal amplification using loop primers; 16(3); pp. 223-229; Jun. 2002.
Needham-Vandevanter et al.; Characterization of an adduct between CC-1065 and a defined oligodeoxynucleotide duplex; Nucleic Acids Research.; 12(15); pp. 6159-6168; Aug. 1984.
Neejara et al.; Rapid detection and differentiation of dengue virus serotypes by NS1 specific reverse transcription loop-mediated isothermal amplification (RT-LAMP) assay in patients presenting to a tertiary care hospital in Hyderabad India; Journal of Virological Methods; 211; pp. 22-31; Jan. 2015.
Ng et al.; The laboratory diagnosis of neisseria gonorrhoeae; Canadian Journal of Infectious Diseases and Medical Microbiology; 16(1); pp. 15-25; Oct. 2005.
Nixon et al.; A novel approach for evaluating the performance of real time quantitative loop-mediated isothermal amplification-based methods; Biomolecular Detection and Quantification; vol. 2; pp. 4-10; Dec. 2014.
Njiru; Loop-mediated isothermal amplification technology: towards point of care diagnostics; Plos Neglected Tropical Diseases; 6(6); e1572; 4 pages; Jun. 2012.
Sievers et al.; Fast, scaleable generation of high-quality protein multiple sequence alignments using clustal omega; Moeicular Systems Biology; 7(1); 539; doi: 10.1038/msb.2011.75; 6 pages; 2011 (the year of publication is sufficiently earlier than the effective U.S. filing date and any foreign priority date so that the particular month of publication is not in issue).
Tanner et al.; Simultaneous multiple target detection in real-time loop-mediated isothermal amplification; Biotechniques; 53(2); pp. 81-89; Aug. 2012.
Trembizki; Direct real-time PCR- based detection of neisseria gonorrhoeae 23S rRNA mutations associated with azithromycin resistance; Journal of Antimicrobial Chemotherapy; 70(12); pp. 3244-3249; Dec. 2015.
Tyagi et al.; Multicolor molecular beacons for allele discrimination; Nature Biotechnology; 16(1); pp. 49-53; Jan. 1998.
Wang et al.; Molecular engineering of DNA: molecular beacons: Angewandle Chemie International Edition; 48(5); pp. 856-870; 34 pages; (Author Manuscript) Jan. 2009.
Wang et al.; Rapid and sensitive detection of shigella spp. And Salmonella spp. by multiple endonuclease restriction real-time loop-mediated isothermal amplification technique; The Journal of Molecular Diagnostics: 17(4); pp. 392-401; Jul. 2015.
Wang et al.; Two methods for increased specificity and sensitivity in loop-mediated isothermal amplification; Molecules; 20(4); pp. 6048-6059; Apr. 2015.
World Health Origanization; The use of commercial loop-mediated isothermal amplification assay (TB-LAMP) for detection of tuberculosis: Expert Group meeting Report Geneva; vol. 2013; pp. 1-50; May 2013.
Xu et al.; A capillary-based multiplexed isothermal nucleic acid-based test for sexually transmitted diseases in patients; Chemical Communications; 52(82); pp. 12187-12190; Sep. 2016.
Xu et al.; Rapid ultrasonic isothermal amplification of DNA with multiplexed melling analysis—applications in the clinical diagnosis of sexually transmitted diseases; Chemical Communications; 51(13); pp. 2589-2592; Jan. 2015.
Yamamoto et al.; Molecular beacon aptamer fluoresces in the presence of Tat protein of HIV-1; Genes to Cells; 5(5); pp. 389-396; May 2000.
Yamamura et al.; Evaluation of a new rapid molecular diagnostic system for plasmodium falciparum combined with DNA filter paper, loop-mediated isothermal amplification, and melting curve analysis; Jpn J. Infect. Dis.; 62(1); pp. 20-25; Jan. 2009.
Zanoli et al.; Isothermal amplification methods for the detection of nucleic acids in microfluidic devices; Biosensors; 3(1); pp. 18-43; Dec. 2012.

(56) References Cited

OTHER PUBLICATIONS

Dedent et al.; U.S. Appl. No. 17/718,025 entitled Polynucleotides for the amplification and detection of chlamydia trachomatis; filed Apr. 11, 2022.
Casolari et al.; U.S. Appl. No. 17/778,486 entitled "Polynucleotides for the amplification and detection of human beta actin," filed May 20, 2022.
GenBank Accession No. NC045512; Severe acute respiratory syndrome coronavirus 2 isolate Wuhan-Hu-1, complete genome; 2 pages; retrieved from the internet (https://www.ncbi.nlm.nih.gov/nuccore/NC_045512.2?report=genbank&from=26523&to=27191) on Apr. 7, 2023.
Marras et al.; Efficiencies of fluorescence resonance energy transfer and contact?mediated quenching in oligonucleotide probes; Nucleic acids research; 30(21); e122; 8 pages; Nov. 1, 2002.
Chaudhry et al.; Detection of Neisseria Gonorrhoeae by polymerase chain reaction (PCR); Indian Journal of Clinical Biochemistry; 14 (2); pp. 135-142; Jul. 1999.
GENEBANK Accession No. CT573023; Mouse DNA Sequence from cline RP23-361611 on chromosone 13, complete sequence; 2 pages; retrieved from the internet (https://www.ncbi.nlm.nih.gov/nuccore/CT573023) on Nov. 2, 2022.
GENEBANK Accession No. LR744041s10; Scyliorhinus canicula genome assembly, chromosome: 12; 1 page; retrieved from the internet (http://www.ncbi.nim.nih.gov/nucore/LR744041) on Oct. 30, 2022.
GENEBANK Accession No. LR812501.1; Danilo aesculapil genome assembly, chromosone: 21; 5 pages; retrieved from the internet (http://www.ncbi.nlm.nih.gov/nuccore/LR812501) on Oct. 30, 2022.
Schachter et al.; Vaginal swabs are the specimens of choice when screening for Chlamydia trachomatis and Neisseria gonorrhoeae: results from a multicenter evaluation of the APTIMA assays for both infections; Sexually transmitted diseases; 32(12); pp. 725-728; Dec. 1, 2005.
Brown et al.; U.S. Appl. No. 18/444,250 entitled "Polynucleotides for the amplification and detection of influenza a," filed Feb. 16, 2024.
Brown et al.; U.S. Appl. No. 18/444,298 entitled "Polynucleotides for the amplification and detection of influenza b," filed Feb. 16, 2024.
Zhang et al., Application of LAMP Technique in Detection of Pathogenic Microorganisms; South China Journal of Preventive Medicine; 33(5): 45-49; Oct. 2007 (with English Abstract).
NEB; Loop-Mediated Isothermal Amplification; 2 pages; retrieved from the internet (https://www.neb.com/en-US/applications/dna-amplification-pcr-and-qpor/isothermal-amplification/loop-media ted-isothermal-amplification-lamp) on Dec. 5, 2024.
New England Biolabs (NEB) 96/97 Catalog: Quick Reference Guide; Nucleic Acids, Linkers and Primers: Random Primers & Transcription Promoter Primers; 4 pages.

\* cited by examiner

SEQUENCE LISTING

<160> NUMBER OF SEQ ID NOS: 117

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctgaaacatc ttagtaagca gagg                                            24

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtgtctagtc ctactcaggt g                                               21

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cctacaaccc cgagccttat caagagattc cctgtgtagc g                         41

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggactcctag ttgaacacat ctggattctc tcctttcgtc tacgg                     45

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctcggttta ggctattccc                                                 20

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aagatggatg atacagggtg atagt                                           25

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atcctttatc ctcaatccta caaccgtagc ggcgagcgaa ag                    42

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agccttatca gctcggtt                                               18

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gacacctgcc gaactg                                                 16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agccttggag agtggt                                                 16

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcctgatcct ttatcctcaa tcctacgaga ttccctgtgt agcg                  44

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcctagttga acacatctgg aaagaaggtg ttgaggtcgg t                     41

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccgtagacga aaggagagaa                                                  20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cctgccgaac tgaaacatc                                                   19

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtgttgagg tcggtctt                                                    18

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cctacaaccc cgagccttat caagagattc cctgtgtagc g                          41

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggatcaggac tcctagttga acacactttc gtctacggga ctatca                     46

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctggaaagat ggatgataca ggg                                              23

```
<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19 ggggttgtagg attgaggata aagg                                          24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggttcactat cggtcattga ctag                                           24

<210> SEQ ID NO 21
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tttctctcct ttcgtctacg ggactatcag gactcctagt tgaacaca                 48

<210> SEQ ID NO 22
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
accgacctca acacctgagt aggttagcct tggagagtgg tctc                     44

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caccctgtat catccatctt tccag                                          25

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgtgaaacct agtctgaatc tggg                                           24

<210> SEQ ID NO 25
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtaggattga ggataaagg                                                19

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cagtactggt tcactatc                                                 18

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tctttctctc ctttcgtcta cctagttgaa cacatctgg                          39

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aacacctgag taggactaga ctagtattta gccttggag                          39

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccctgtatca tccatctttt                                                19

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgaaacctag tctgaatctg                                                20

<210> SEQ ID NO 31
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggagcaattg tttcgacg                                                    18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgtctcagtc ccagtgtt                                                    18

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcccaaatat cgccacattc gggcggaagg gttagtaatg                            40

<210> SEQ ID NO 34
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gacctttcgg ttaagggaga gtcgacgtca tagccttggt ag                         42

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgtttccaac cgttattccc                                                  20

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agttggtggg gtaaaggc                                                    18

<210> SEQ ID NO 37
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
ttagtggcgg aagggttag                                                    19

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tctcaatccg cctagacg                                                     18

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aacgttactc ggatgcccaa atggaataac ggttggaaac gg                          42

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aggacctttc ggttaaggga gatagccttg gtaggccttt ac                          42

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atcgccacat tcggtattag c                                                 21

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtgatatcag ctagttggtg gg                                                22

<210> SEQ ID NO 43
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 43
gaacggagca attgt                                                      15

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctgatatcac atagactctc                                                 20

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccgtttccaa ccgttattct cgacgattgt ttagtg                               36

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
taccgaatgt ggcgatattt cgaaaggtcc taagatc                              37

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ctatgcatta ctaacccttc                                                 20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
catccgagta acgttaaag                                                  19

<210> SEQ ID NO 49
<211> LENGTH: 38
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 49
cgcgatcagg actcctagtt gaacacatct ggatcgcg                               38

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
cgtccaggac tcctagttga acacatctgg acg                                    33

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
cgcgactcag gactcctagt tgaacacatc tggagtcgcg                             40

<210> SEQ ID NO 52
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
cgcgagtagg attgaggata aaggatcagg actcgcg                                37

<210> SEQ ID NO 53
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
cgcgcacatc tggaaagatg gatgatacag ggtgcgcg                               38

<210> SEQ ID NO 54
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
cgcgatccgg ataaaggatc aggactccta gttgggatcg cg                          42

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic

```
                            probe

<400> SEQUENCE: 55
cgcgatcaga ccgacctcaa cacctgagat cgcg                          34

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
cgcagtgaga gaaagaccga cctcaacact gcg                           33

<210> SEQ ID NO 57
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
cgcgatcctg tgtagcggcg agcgaaagat cgcg                          34

<210> SEQ ID NO 58
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
cgcgatcatc cgagtaacgt taaagaaggg gatcgcg                       37

<210> SEQ ID NO 59
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
cgcgatctgg cgatatttgg gcatccgaga tcgcg                         35

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cgtaacagct caccaatcg                                           19

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 61
tacgcagtta cgcctcaa                                                                18

<210> SEQ ID NO 62
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgctccttcc ggtacacctt tcgataagac acgcggtag                                         39

<210> SEQ ID NO 63
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aatctccctc gccgtaagcc gactaaccca gggaagacg                                         39

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ctctgctgaa tactacgctc tc                                                           22

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
caaggtttcc agggtcaagc                                                              20

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccaaggtttc cagggtcaa                                                               19

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 67
ccgaagattc cccttgatcg                                                  20

<210> SEQ ID NO 68
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ctgctccatc gtctacgcag tttgctcgtc ttccctgggt t                           41

<210> SEQ ID NO 69
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
acggagtaag ttaagcacgc ggtgcggatt tgcctactaa ccg                         43

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ctcaacttag gggccgact                                                   19

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
acgattggaa gagtccgtag ag                                               22

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tatgcaaagc gacacctg                                                    18

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
```

```
ttagccttgg agagtggtc                                                  19

<210> SEQ ID NO 74
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tcctcaatcc tacaaccccg agcgaagaga ttccctgtgt ag                        42

<210> SEQ ID NO 75
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gggtgatagt cccgtagacg aacgtgtcta gtcctactca gg                        42

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gagagaaaga ccgacctcaa c                                               21

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
agagattccc tgtgtagcg                                                  19

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ccttcacagt actggttcac                                                 20

<210> SEQ ID NO 79
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
```
ctctcctttc gtctacggga ctaaccgagc tgataaggct                           40

<210> SEQ ID NO 80
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
aagaccgacc tcaacacctg attagccttg gagagtggtc                           40

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gttcaactag gagtcctgat cc                                              22

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gtaggactag acacgtgaaa cc                                              22

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
catgctgaat acataggtat gc                                              22

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tctagtccta ctcaggtgtt                                                 20

<210> SEQ ID NO 85
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tcctttatcc tcaatcctac aacccatcga agagattccc tgtg                      44

<210> SEQ ID NO 86
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
actcctagtt gaacacatct ggaatctttc tctcctttcg tctac            45

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tggatgatac agggtgatag tc            22

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gggttgtagg attgaggata aagg            24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ggttcactat cggtcattga ctag            24

<210> SEQ ID NO 90
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tttctctcct ttcgtctacg ggactatcag gactcctagt tgaacaca            48

<210> SEQ ID NO 91
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
accgacctca acacctgagt aggttagcct tggagagtgg tctc            44

```
<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
caccctgtat catccatctt tccag                                          25

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cgtgaaacct agtctgaatc tggg                                           24

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
cgaactgaaa catcttagta agcag                                          25

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ctcctttcgt ctacgggact a                                              21

<210> SEQ ID NO 96
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
atcagctcgg tttaggctat tcccgaaaag aaatcgaaga gattccctg                49

<210> SEQ ID NO 97
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gctcggggtt gtaggattga ggatacctgt atcatccatc tttccagat                49
```

```
<210> SEQ ID NO 98
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ctttcgctcg ccgctac                                                  17

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ggatcaggac tcctagttga acac                                          24

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cttacaagcg gtcggaga                                                 18

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
caggtactag ttcggtcctc                                               20

<210> SEQ ID NO 102
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
cccttaacct cgccgtttag ccccgtaagg gtcaaggtt                          39

<210> SEQ ID NO 103
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ccggagcgaa agcgagtttg ctcacttggt ttcgtgtc                           38

<210> SEQ ID NO 104
```

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
tccctggctc atcatgca                                                 18

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gagcgaagag tcgtttggtt                                               20

<210> SEQ ID NO 106
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
cgcgatcaga tccatggcat aagtaacgga tcgcg                              35

<210> SEQ ID NO 107
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
cgcgatcggt gaagatccat ggcataagta acgcgatcgc g                       41

<210> SEQ ID NO 108
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
cgcgatccat ggcataagta acgataaagg gagtgaggat cgcg                    44

<210> SEQ ID NO 109
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
cgcgatcatg acggagtaag ttaagcacgc gatcgcg                            37

<210> SEQ ID NO 110
<211> LENGTH: 36
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
cgcgatgtct ggaaagatgg atgatacagc atcgcg                              36

<210> SEQ ID NO 111
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
cgcgatctga ggataaagga tcaggactcg atcgcg                              36

<210> SEQ ID NO 112
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112
cgcgatccct gtgtagcggc gagcgagatc gcg                                 33

<210> SEQ ID NO 113
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
cgcgatcgca aaaggcacgc cgtcaagatc gcg                                 33

<210> SEQ ID NO 114
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
cggctcgggg ttgtaggatt gaggatacga gccg                                34

<210> SEQ ID NO 115
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
ccggagccta aaccccgag ccttatcagc tccgg                                35

<210> SEQ ID NO 116
<211> LENGTH: 33
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 116
cgcgcagctc ggtttaggct attcccctgc gcg                                    33

<210> SEQ ID NO 117
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
cgcggtctct cctttcgtct acgggaccgc g                                      31
```

POLYNUCLEOTIDES FOR THE AMPLIFICATION AND DETECTION OF CHLAMYDIA TRACHOMATIS

CROSS REFERENCE TO RELATED APPLICATIONS

This application claims the benefit of U.S. Provisional Patent Application No. 62/420,488, filed 10 Nov. 2016, the contents of which are incorporated herein by reference.

GOVERNMENT LICENSE RIGHTS

This invention was made with government support under contract number HR0011-11-2-0006 awarded by the Department of Defense. The government has certain rights in the invention.

SEQUENCE LISTING

The instant application contains a Sequence Listing which has been submitted via EFS-Web and is hereby incorporated by reference in its entirety. Said ASCII copy, created on Apr. 19, 2021, is named TSM-027WOUS_Sequence_Listing.txt, and is 26,807 bytes in size.

FIELD OF THE INVENTION

The present invention relates to the fields of molecular biology and nucleic acid chemistry. The invention provides methods and reagents for detecting pathogens, such as *Chlamydia trachomatis* and accordingly, also relates to the fields of medical diagnostics and prognostics. In particular, the invention relates to polynucleotides and methods for amplifying and detecting *Chlamydia trachomatis*.

BACKGROUND OF THE INVENTION

There is an urgent need for the development of a rapid, affordable, sample-in answer-out point of care (POC) diagnostic platform for sexually transmitted infections (STIs). The World Health Organization (WHO) estimates that more than 499 million new cases of curable STIs, namely those due to *Neisseria gonorrhoeae* (NG), *Chlamydia trachomatis* (CT), *Trichomonas vaginalis* (TV) and *Syphilis* occur every year worldwide in men and women aged 15-49 years, causing significant morbidity and mortality. Untreated gonococcal and chlamydial infections in women in sub-Saharan Africa have been implicated as the cause of up to 85% of infertility among women seeking infertility intervention.

*C. trachomatis* is responsible for the most common STD in the US. *Chlamydia* can cause urethritis in men and pelvic inflammatory disease, ectopic pregnancy and infertility in women.

Asymptomatic infections are common both in men and women which warrants screenings to prevent the spread of the disease (as recommended by the CDC).

SUMMARY

The present invention encompasses, in some embodiments, a composition comprising a set of polynucleotides selected from the group consisting of Set-1 through Set-58. In some embodiments, the composition further comprises a probe. In some embodiments, the probe comprises a label. In some embodiments, the probe is a labeled polynucleotide. In some embodiments, the probe is a labeled polynucleotide having a sequence selected from the group consisting of SEQ ID NO: 49, SEQ ID NO: 50, and SEQ ID NO: 51 and the set of polynucleotides is selected from the group consisting of Set-5, Set-15, Set-24, and Set-32. In some embodiments, the probe is a labeled polynucleotide having a sequence selected from the group consisting of SEQ ID NO: 49, SEQ ID NO: 50, SEQ ID NO: 51, SEQ ID NO: 52, SEQ ID NO: 53, and SEQ ID NO: 54 and the set of polynucleotides is selected from the group consisting of Set-1, Set-2, Set-3, Set-4, Set-10, Set-11, Set-12, Set-13, Set-14, Set-20, Set-21, Set-22, Set-23, Set-29, Set-30, Set-31, Set-39, Set-40, Set-41, Set-43,47, Set-48, Set-49, Set-50, Set-54, Set-55, Set-56, and Set-57. In some embodiments, the probe is a labeled polynucleotide having a sequence selected from the group consisting of SEQ ID NO: 55 and SEQ ID NO: 56 and the set of polynucleotides is selected from the group consisting of Set-3, Set-4, Set-5, Set-6, Set-13, Set-14, Set-15, Set-16, Set-22, Set-23, Set-24, Set-25, Set-30, Set-31, Set-32, Set-33, Set-39, Set-40, Set-47, Set-48, Set-54, and Set-55. In some embodiments, the probe is a labeled polynucleotide having a sequence SEQ ID NO: 57 and the set of polynucleotides is selected from the group consisting of Set-1, Set-2, Set-3, Set-4, Set-10, Set-11, Set-12, Set-13, Set-14, Set-20, Set-21, Set-22, Set-23, Set-29, Set-30, Set-31, Set-39, Set-41, Set-43, Set-47, Set-49, Set-50, Set-54, Set-56, and Set-57. In some embodiments, the probe is a labeled polynucleotide having a sequence selected from the group consisting of SEQ ID NO: 58 and SEQ ID NO: 59and the set of polynucleotides is selected from the group consisting of Set-7, Set-8, Set-9, Set-17, Set-18, Set-19, Set-26, Set-27, Set-28, Set-34, Set-35, and Set-36. In some embodiments, the probe is a labeled polynucleotide having a sequence selected from the group consisting of SEQ ID NO: 106, SEQ ID NO: 107, and SEQ ID NO: 108 and the set of polynucleotides is selected from the group consisting of Set-37, Set-45, and Set-52. In some embodiments, the probe is a labeled polynucleotide having a sequence SEQ ID NO: 109and the set of polynucleotides is selected from the group consisting of Set-38, Set-46, and Set-53. In some embodiments, the probe is a labeled polynucleotide having a sequence SEQ ID NO: 110 and the set of polynucleotides is selected from the group consisting of Set-1, Set-2, Set-3, Set-4, Set-5, Set-6, Set-10, Set-11, Set-12, Set-13, Set-14, Set-15, Set-16, Set-20, Set-21, Set-22, Set-23, Set-24, Set-25, Set-29, Set-30, Set-31, Set-32, Set-33, Set-40, Set-43, Set-39, Set-41, Set-47, Set-48, Set-49, Set-50, Set-54, Set-55, Set-56, and Set-57. In some embodiments, the probe is a labeled polynucleotide having a sequence selected from the group consisting of SEQ ID NO: 111, SEQ ID NO: 114, and SEQ ID NO: 115, and the set of polynucleotides is selected from the group consisting of Set-1, Set-2, Set-3, Set-4, Set-10, Set-11, Set-12, Set-13, Set-14, Set-20, Set-21, Set-22, Set-23, Set-29, Set-30, Set-31, Set-40, Set-43, Set-39, Set-41, Set-47, Set-48, Set-49, Set-50, Set-54, Set-55, Set-56, and Set-57. In some embodiments, the probe is a labeled polynucleotide having a sequence SEQ ID NO: 112 and the set of polynucleotides is selected from the group consisting of Set-1, Set-3, Set-4, Set-10, Set-11, Set-13, Set-14, Set-20, Set-22, Set-23, Set-30, Set-31, Set-39, Set-41, Set-43, Set-47, Set-49, Set-50, Set-54, Set-56, and Set-57. In some embodiments, the probe is a labeled polynucleotide having a sequence SEQ ID NO: 113 and the set of polynucleotides is selected from the group consisting of Set-44, Set-51, and Set-58. In some embodiments, the probe is a labeled polynucleotide having a sequence SEQ ID NO: 116 and the set of polynucleotides is selected from the group consisting of Set-1, Set-2, Set-3, Set-4, Set-10, Set-11, Set-12, Set-13, Set-14, Set-20, Set-21, Set-22, Set-23, Set-29, Set-30, Set-31, Set-39, Set-41, Set-43, Set-47, Set-49, Set-50, Set-54, Set-56, and Set-57. In some embodiments, the probe is a labeled polynucleotide having a sequence SEQ ID NO: 117 and the set of polynucleotides is selected from the group consisting of Set-1, Set-2, Set-3, Set-4, Set-5, Set-6, Set-10, Set-11, Set-12, Set-13, Set-14, Set-15, Set-16, Set-20, Set-21, Set-22, Set-23, Set-24, Set-25, Set-29, Set-30, Set-31, Set-32, Set-33, Set-39, Set-40, Set-41, Set-47, Set-48, Set-49, Set-54, Set-55, and Set-56.

In some embodiments, the label is a fluorophore. In some embodiments, the fluorophore is covalently attached to a terminus of the polynucleotide. In some embodiments, the probe is a molecular beacon comprising a quencher. In some embodiments, the fluorophore is FAM and the quencher is BHQ1. In other embodiments, the fluorophore is ATTO 565 or Alexa 594 and the quencher is BHQ1 or BHQ2.

Also provided herein is a molecular beacon comprising a fluorophore, a quencher, and a polynucleotide, wherein the polynucleotide is selected from the group consisting of: SEQ ID NO: 49 through SEQ ID NO: 59 and SEQ ID NO: 106 through SEQ ID NO: 117. In some embodiments, the fluorophore is FAM and the quencher is BHQ1. In other embodiments, the fluorophore is ATTO 565 or Alexa 594 and the quencher is BHQ1 or BHQ2.

Also provided herein is a method of detecting *Chlamydia trachomatis* in a test sample, the method comprising: (a) extracting nucleic acid from the test sample; (b) amplifying a target sequence by reacting the nucleic acid extracted in step (a) with a reaction mixture comprising a strand displacement DNA polymerase and a sequence-specific primer set, wherein said sequence-specific primer set is selected from the group consisting of Set-1 through Set-36; and (c) detecting the presence or absence of an amplified product of step (b); wherein the presence of said amplification product is indicative of the presence of *Chlamydia trachomatis* in the test sample.

In some embodiments of the method, the amplification in step (b) of the target sequence is performed at between about 60° C. and about 67° C. for less than 30 minutes. In some embodiments of the method, the amplification step is performed for less than 15 minutes. In some embodiments of the method, the amplification step is performed for less than nine minutes.

In some embodiments of the method, detecting the presence or absence of the amplification product comprises hybridizing the amplified product with a probe comprising a polynucleotide attached to a label.

In some embodiments of the method, the polynucleotide comprises a sequence selected from the group consisting of SEQ ID NO: 49, SEQ ID NO: 50, and SEQ ID NO: 51 and the set of polynucleotides is selected from the group consisting of Set-5, Set-15, Set-24, and Set-32. In some embodiments of the method, the polynucleotide comprises a sequence selected from the group consisting of SEQ ID NO: 49, SEQ ID NO: 50, SEQ ID NO: 51, SEQ ID NO: 52, SEQ ID NO: 53, and SEQ ID NO: 54 and the set of polynucleotides is selected from the group consisting of Set-1, Set-2, Set-3, Set-4, Set-10, Set-11, Set-12, Set-13, Set-14, Set-20, Set-21, Set-22, Set-23, Set-29, Set-30, Set-31, Set-39, Set-40, Set-41, Set-43,47, Set-48, Set-49, Set-50, Set-54, Set-55, Set-56, and Set-57. In some embodiments of the method, the polynucleotide comprises a sequence selected from the group consisting of SEQ ID NO: 55 and SEQ ID NO: 56 and the set of polynucleotides is selected from the group consisting of Set-3, Set-4, Set-5, Set-6, Set-13, Set-14, Set-15, Set-16, Set-22, Set-23, Set-24, Set-25, Set-30, Set-31, Set-32, Set-33, Set-39, Set-40, Set-47, Set-48, Set-54, and Set-55. In some embodiments of the method, the polynucleotide comprises a sequence SEQ ID NO: 57 and the set of polynucleotides is selected from the group consisting of Set-1, Set-2, Set-3, Set-4, Set-10, Set-11, Set-12, Set-13, Set-14, Set-20, Set-21, Set-22, Set-23, Set-29, Set-30, Set-31, Set-39, Set-41, Set-43, Set-47, Set-49, Set-50, Set-54, Set-56, and Set-57. In some embodiments of the method, the polynucleotide comprises a sequence selected from the group consisting of SEQ ID NO: 58 and SEQ ID NO: 59 and the set of polynucleotides is selected from the group consisting of Set-7, Set-8, Set-9, Set-17, Set-18, Set-19, Set-26, Set-27, Set-28, Set-34, Set-35, and Set-36. In some embodiments of the method, the polynucleotide comprises a sequence selected from the group consisting of SEQ ID NO: 106, SEQ ID NO: 107, and SEQ ID NO: 108 and the set of polynucleotides is selected from the group consisting of Set-37, Set-45, and Set-52. In some embodiments of the method, the polynucleotide comprises a sequence SEQ ID NO: 109and the set of polynucleotides is selected from the group consisting of Set-38, Set-46, and Set-53. In some embodiments of the method, the polynucleotide comprises a sequence SEQ ID NO: 110 and the set of polynucleotides is selected from the group consisting of Set-1, Set-2, Set-3, Set-4, Set-5, Set-6, Set-10, Set-11, Set-12, Set-13, Set-14, Set-15, Set-16, Set-20, Set-21, Set-22, Set-23, Set-24, Set-25, Set-29, Set-30, Set-31, Set-32, Set-33, Set-40, Set-43, Set-39, Set-41, Set-47, Set-48, Set-49, Set-50, Set-54, Set-55, Set-56, and Set-57. In some embodiments of the method, the polynucleotide comprises a sequence selected from the group consisting of SEQ ID NO: 111, SEQ ID NO: 114, and SEQ ID NO: 115, and the set of polynucleotides is selected from the group consisting of Set-1, Set-2, Set-3, Set-4, Set-10, Set-11, Set-12, Set-13, Set-14, Set-20, Set-21, Set-22, Set-23, Set-29, Set-30, Set-31, Set-40, Set-43, Set-39, Set-41, Set-47, Set-48, Set-49, Set-50, Set-54, Set-55, Set-56, and Set-57. In some embodiments of the method, the polynucleotide comprises a sequence SEQ ID NO: 112 and the set of polynucleotides is selected from the group consisting of Set-1, Set-3, Set-4, Set-10, Set-11, Set-13, Set-14, Set-20, Set-22, Set-23, Set-30, Set-31, Set-39, Set-41, Set-43, Set-47, Set-49, Set-50, Set-54, Set-56, and Set-57. In some embodiments of the method, the polynucleotide comprises a sequence SEQ ID NO: 113 and the set of polynucleotides is selected from the group consisting of Set-44, Set-51, and Set-58. In some embodiments of the method, the polynucleotide comprises a sequence SEQ ID NO: 116 and the set of polynucleotides is selected from the group consisting of Set-1, Set-2, Set-3, Set-4, Set-10, Set-11, Set-12, Set-13, Set-14, Set-20, Set-21, Set-22, Set-23, Set-29, Set-30, Set-31, Set-39, Set-41, Set-43, Set-47, Set-49, Set-50, Set-54, Set-56, and Set-57. In some embodiments of the method, the polynucleotide comprises a sequence SEQ ID NO: 117 and the set of polynucleotides is selected from the group consisting of Set-1, Set-2, Set-3, Set-4, Set-5, Set-6, Set-10, Set-11, Set-12, Set-13, Set-14, Set-15, Set-16, Set-20, Set-21, Set-22, Set-23, Set-24, Set-25, Set-29, Set-30, Set-31, Set-32, Set-33, Set-39, Set-40, Set-41, Set-47, Set-48, Set-49, Set-54, Set-55, and Set-56.

In some embodiments of the method, the probe is a molecular beacon. In some embodiments of the method, the reaction mixture further comprises a reverse transcriptase.

In some embodiments of the method, *Chlamydia trachomatis* is present in the test sample at a concentration of ≤100 IFU/mL. In some embodiments of the method, *Chla-*

*mydia trachomatis* is present in the test sample at a concentration of ≤50 IFU/mL. In some embodiments of the method, *Chlamydia trachomatis* is present in the test sample at a concentration of ≤5 IFU/mL.

In some embodiments of the method, *Chlamydia trachomatis* is present in the test sample at a concentration of ≤2 IFU/ml and the amplification step is performed for less than 15 minutes.

Also provided herein is a kit comprising the composition of claim 1 and amplification reagents. In some embodiments of the kit, the amplification reagents comprise a strand displacement polymerase.

Also provided herein, in some embodiments, is a method of detecting *Chlamydia trachomatis* in a test sample, the method comprising: (a) extracting nucleic acid from the test sample; (b) amplifying a target sequence by reacting the nucleic acid extracted in step (a) for less than twenty minutes with a reaction mixture comprising a strand displacement DNA polymerase and a sequence-specific LAMP primer set; and (c) detecting the presence or absence of an amplified product of step (b); wherein the presence of said amplification product is indicative of the presence of *Chlamydia trachomatis* in the test sample.

In some embodiments of the method, the nucleic acid is reacted with the reaction mixture for less than fifteen minutes.

In some embodiments of the method, the target sequence is located in the 16S ribosomal subunit of *Chlamydia trachomatis*. In some embodiments of the method, the target sequence is located in the 23S ribosomal subunit of *Chlamydia trachomatis*.

In some embodiments of the method, the LAMP primer set consists of a forward inner primer (FIP), a backward inner primer (BIP), a forward loop primer (LF) and a backward loop primer (LB). In some embodiments of the method, the LAMP primer set consists of a forward inner primer (FIP), a backward inner primer (BIP), a forward outer primer (F3) and a backward outer primer (B3). In some embodiments of the method, the LAMP primer set consists of a forward inner primer (FIP), a backward inner primer (BIP), a forward outer primer (F3), a backward outer primer (B3), a forward loop primer (LF) and a backward loop primer (LB).

In some embodiments of the method, *Chlamydia trachomatis* is present in the test sample at a concentration of ≤100 IFU/mL. In some embodiments of the method, *Chlamydia trachomatis* is present in the test sample at a concentration of ≤50 IFU/mL. In some embodiments of the method, *Chlamydia trachomatis* is present in the test sample at a concentration of ≤5 IFU/mL.

In some embodiments of the method, the test sample comprises one or more other microorganisms in addition to *Chlamydia trachomatis*, and wherein the target sequence from *Chlamydia trachomatis* is preferentially amplified over a polynucleotide sequence from the one or more other microorganisms.

In some embodiments, the invention provides a nucleic acid sequence at least 90%, at least 95%, at least 96%, at least 97%, at least 98%, at least 99%%, at least 99.1%, at least 99.2%, at least 99.3%, at least 99.4%, at least 99.5%, at least 99.6%, at least 99.7%, at least 99.8% or at least 99.9% identical to SEQ ID NOs 1-59 and methods of using those nucleic acid sequences to detect *Chlamydia trachomatis* in a test sample.

DETAILED DESCRIPTION

Detecting low concentrations of species (down to a few molecules or microorganisms in a sample) is a challenge in medicine. The present invention relates to the selective detection of *Chlamydia trachomatis*. In particular, based on new detection strategies utilizing nucleic acid amplification, particularly RT-LAMP, and molecular beacon detection, *Chlamydia* infections can be diagnosed using the methods and reagents described herein. Using RNA (either ribosomal RNA (rRNA) or messenger RNA) as the target regions provides multiple copies of the target per *C. trachomatis* genome. Accordingly, this facilitates the detection of *C. trachomatis* in samples utilizing the approaches described herein relative to techniques that target genomic DNA, even when present in multiple copies per genome. In addition, the molecular beacon detection reagents described herein provide additional specificity, failing to bind, in most cases, to off target amplified DNA, thereby minimizing the occurrence of, e.g., false positives. This specificity is illustrated in, inter alia, Example 4 provided below. Many other features of the invention are also described herein.

As used herein, "nucleic acid" includes both DNA and RNA, including DNA and RNA containing non-standard nucleotides. A "nucleic acid" contains at least one polynucleotide (a "nucleic acid strand"). A "nucleic acid" may be single-stranded or double-stranded. The term "nucleic acid" refers to nucleotides and nucleosides which make up, for example, deoxyribonucleic acid (DNA) macromolecules and ribonucleic acid (RNA) macromolecules. Nucleic acids may be identified by the base attached to the sugar (e.g., deoxyribose or ribose).

As used herein, a "polynucleotide" refers to a polymeric chain containing two or more nucleotides, which contain deoxyribonucleotides, ribonucleotides, and/or their analog, such as those containing modified backbones (e.g. peptide nucleic acids (PNAs) or phosphorothioates) or modified bases. "Polynucleotides" includes primers, oligonucleotides, nucleic acid strands, etc. A polynucleotide may contain standard or non-standard nucleotides. Thus the term includes mRNA, tRNA, rRNA, ribozymes, DNA, cDNA, recombinant nucleic acids, branched nucleic acids, plasmids, vectors, probes, primers, etc. Typically, a polynucleotide contains a 5' phosphate at one terminus ("5' terminus") and a 3' hydroxyl group at the other terminus ("3' terminus") of the chain. The most 5' nucleotide of a polynucleotide may be referred to herein as the "5' terminal nucleotide" of the polynucleotide. The most 3' nucleotide of a polynucleotide may be referred to herein as the "3' terminal nucleotide" of the polynucleotide. Where nucleic acid of the invention takes the form of RNA, it may or may not have a 5' cap.

LAMP is a nucleic acid amplification method that relies on auto-cycle strand-displacement DNA synthesis performed by Bst DNA polymerase, or other strand displacement polymerases. The amplified products are stem-loop structures with several repeated sequences of the target, and have multiple loops. The principal merit of this method is that denaturation of the DNA template is not required, and thus the LAMP reaction can be conducted under isothermal conditions (ranging from 60 to 67° C.). LAMP requires only one enzyme and four types of primers that recognize six distinct hybridization sites in the target sequence. The reaction can be accelerated by the addition of two additional primers. The method produces a large amount of amplified product, resulting in easier detection, such as detection by visual judgment of the turbidity or fluorescence of the reaction mixture.

In brief, the reaction is initiated by annealing and extension of a pair of 'loop-forming' primers (forward and backward inner primers, FIP and BIP, respectively), followed by annealing and extension of a pair of flanking primers (F3 and B3). Extension of these primers results in strand-displacement of the loop-forming elements, which fold up to form terminal hairpin-loop structures. Once these key structures have appeared, the amplification process becomes self-sustaining, and proceeds at constant temperature in a continuous and exponential manner (rather than a cyclic manner, like PCR) until all of the nucleotides (dATP, dTTP, dCTP & dGTP) in the reaction mixture have been incorporated into the amplified DNA. Optionally, an additional pair of primers can be included to accelerate the reaction. These primers, termed Loop primers, hybridize to non-inner primer bound terminal loops of the inner primer dumbbell shaped products.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

LAMP allows amplification of target DNA sequences with higher sensitivity and specificity than PCR, often with reaction times of below 30 minutes, which is equivalent to the fastest real-time PCR tests. The target sequence which is amplified is typically 200-300 base-pairs (bp) in length, and the reaction relies upon recognition of between 120 bp and 160 bp of this sequence by several primers simultaneously during the amplification process. This high level of stringency makes the amplification highly specific, such that the appearance of amplified DNA in a reaction occurs only if the entire target sequence was initially present.

Applications for LAMP have been further extended to include detection of RNA molecules by addition of Reverse Transcriptase enzyme (RT). By including RNA detection, the types of targets for which LAMP can be applied are also expanded and add the ability to additionally target RNA based viruses, important regulatory non-coding RNA (sRNA, miRNA), and RNA molecules that have been associated with particular disease or physiological states. The ability to detect RNA also has the potential to increase assay sensitivity, for instance in choosing highly expressed, stable, and/or abundant messenger RNA (mRNA) or ribosomal RNA (rRNA) targets. This preliminary phase of amplification involves the reverse transcription of RNA molecules to complementary DNA (cDNA). The cDNA then serves as template for the strand displacing DNA polymerase. Use of a thermostable RT enzyme (i.e., NEB RTx) enables the reaction to be completed at a single temperature and in a one step, single mix reaction.

A "target sequence," as used herein, means a nucleic acid sequence of *Chlamydia trachomatis*, or complement thereof, that is amplified, detected, or both amplified and detected using one or more of the polynucleotides herein provided. Additionally, while the term target sequence sometimes refers to a double stranded nucleic acid sequence, those skilled in the art will recognize that the target sequence can also be single stranded, e.g., RNA. A target sequence may be selected that is more or less specific for a particular organism. For example, the target sequence may be specific to an entire genus, to more than one genus, to a species or subspecies, serogroup, auxotype, serotype, strain, isolate or other subset of organisms.

The speed, specificity and sensitivity of the primers/probe compositions and method described herein result from several aspects. Exemplary primers for use in the compositions and methods according to the present invention include:

TABLE 1

Primer Sequences

| Target | Sequence ID | Sequence (5' to 3') |
|---|---|---|
| 23S | SEQ ID NO: 1 | CTGAAACATCTTAGTAAGCAGAGG |
| 23S | SEQ ID NO: 2 | GTGTCTAGTCCTACTCAGGTG |
| 23S | SEQ ID NO: 3 | CCTACAACCCCGAGCCTTATCAAGAGATTCC CTGTGTAGCG |
| 23S | SEQ ID NO: 4 | GGACTCCTAGTTGAACACATCTGGATTCTCT CCTTTCGTCTACGG |
| 23S | SEQ ID NO: 5 | GCTCGGTTTAGGCTATTCCC |
| 23S | SEQ ID NO: 6 | AAGATGGATGATACAGGGTGATAGT |
| 23S | SEQ ID NO: 7 | ATCCTTTATCCTCAATCCTACAACC GTA GCG GCG AGC GAA AG |
| 23S | SEQ ID NO: 8 | AGCCTTATCAGCTCGGTT |
| 23S | SEQ ID NO: 9 | GAC ACC TGC CGA ACT G |
| 23S | SEQ ID NO: 10 | AGC CTT GGA GAG TGG T |
| 23S | SEQ ID NO: 11 | TCC TGA TCC TTT ATC CTC AAT CCT ACG AGA TTC CCT GTG TAG CG |
| 23S | SEQ ID NO: 12 | TCC TAG TTG AAC ACA TCT GGA AAG AAG GTG TTG AGG TCG GT |
| 23S | SEQ ID NO: 13 | CCG TAG ACG AAA GGA GAG AA |
| 23S | SEQ ID NO: 14 | CCTGCCGAACTGAAACATC |
| 23S | SEQ ID NO: 15 | GGTGTTGAGGTCGGTCTT |
| 23S | SEQ ID NO: 16 | CCTACAACCCCGAGCCTTATCAAGAGATTCC CTGTGTAGCG |
| 23S | SEQ ID NO: 17 | GGATCAGGACTCCTAGTTGAACACACTTTCG TCTACGGGACTATCA |
| 23S | SEQ ID NO: 18 | CTGGAAAGATGGATGATACAGGG |
| 23S | SEQ ID NO: 19 | GGGTTGTAGGATTGAGGATAAAGG |
| 23S | SEQ ID NO: 20 | GGTTCACTATCGGTCATTGACTAG |
| 23S | SEQ ID NO: 21 | TTTCTCTCCTTTCGTCTACGGGACTATCAGG ACTCCTAGTTGAACACA |
| 23S | SEQ ID NO: 22 | ACCGACCTCAACACCTGAGTAGGTTAGCCTT GGAGAGTGGTCTC |
| 23S | SEQ ID NO: 23 | CACCCTGTATCATCCATCTTTCCAG |
| 23S | SEQ ID NO: 24 | CGTGAAACCTAGTCTGAATCTGGG |
| 23S | SEQ ID NO: 25 | GTAGGATTGAGGATAAAGG |

TABLE 1-continued

Primer Sequences

| Target | Sequence ID | Sequence (5' to 3') |
|---|---|---|
| 23S | SEQ ID NO: 26 | CAGTACTGGTTCACTATC |
| 23S | SEQ ID NO: 27 | TCTTTCTCTCCTTTCGTCTACCTAGTTGAACACATCTGG |
| 23S | SEQ ID NO: 28 | AACACCTGAGTAGGACTAGACTAGTATTTAGCCTTGGAG |
| 23S | SEQ ID NO: 29 | CCCTGTATCATCCATCTTT |
| 23S | SEQ ID NO: 30 | TGAAACCTAGTCTGAATCTG |
| 16S | SEQ ID NO: 31 | GGAGCAATTGTTTCGACG |
| 16S | SEQ ID NO: 32 | TGTCTCAGTCCCAGTGTT |
| 16S | SEQ ID NO: 33 | GCCCAAATATCGCCACATTCGGGCGGAAGGGTTAGTAATG |
| 16S | SEQ ID NO: 34 | GACCTTTCGGTTAAGGGAGAGTCGACGTCATAGCCTTGGTAG |
| 16S | SEQ ID NO: 35 | CGTTTCCAACCGTTATTCCC |
| 16S | SEQ ID NO: 36 | AGTTGGTGGGTAAAGGC |
| 16S | SEQ ID NO: 37 | TTAGTGGCGGAAGGGTTAG |
| 16S | SEQ ID NO: 38 | TCTCAATCCGCCTAGACG |
| 16S | SEQ ID NO: 39 | AACGTTACTCGGATGCCCAAATGGAATAACGGTTGGAAACGG |
| 16S | SEQ ID NO: 40 | AGGACCTTTCGGTTAAGGGAGATAGCCTTGGTAGGCCTTTAC |
| 16S | SEQ ID NO: 41 | ATCGCCACATTCGGTATTAGC |
| 16S | SEQ ID NO: 42 | GTGATATCAGCTAGTTGGTGGG |
| 16S | SEQ ID NO: 43 | GAACGGAGCAATTGT |
| 16S | SEQ ID NO: 44 | CTGATATCACATAGACTCTC |
| 16S | SEQ ID NO: 45 | CCGTTTCCAACCGTTATTCTCGACGATTGTTTAGTG |
| 16S | SEQ ID NO: 46 | TACCGAATGTGGCGATATTTCGAAAGGTCCTAAGATC |
| 16S | SEQ ID NO: 47 | CTA TGC ATT ACT AAC CCT TC |
| 16S | SEQ ID NO: 48 | CATCCGAGTAACGTTAAAG |
| 23S | SEQ ID NO: 60 | CGTAACAGCTCACCAATCG |
| 23S | SEQ ID NO: 61 | TACGCAGTTACGCCTCAA |
| 23S | SEQ ID NO: 62 | CGCTCCTTCCGGTACACCTTTCGATAAGACACGCGGTAG |
| 23S | SEQ ID NO: 63 | AATCTCCCTCGCCGTAAGCCGACTAACCCAGGGAAGACG |
| 23S | SEQ ID NO: 64 | CTCTGCTGAATACTACGCTCTC |
| 23S | SEQ ID NO: 65 | CAAGGTTTCCAGGGTCAAGC |
| 23S | SEQ ID NO: 66 | CCAAGGTTTCCAGGGTCAA |
| 23S | SEQ ID NO: 67 | CCGAAGATTCCCCTTGATCG |
| 23S | SEQ ID NO: 68 | CTGCTCCATCGTCTACGCAGTTTGCTCGTCTTCCCTGGGTT |
| 23S | SEQ ID NO: 69 | ACGGAGTAAGTTAAGCACGCGGTGCGGATTTGCCTACTAACCG |
| 23S | SEQ ID NO: 70 | CTCAACTTAGGGGCCGACT |
| 23S | SEQ ID NO: 71 | ACGATTGGAAGAGTCCGTAGAG |
| 23S | SEQ ID NO: 72 | TATGCAAAGCGACACCTG |
| 23S | SEQ ID NO: 73 | TTAGCCTTGGAGAGTGGTC |
| 23S | SEQ ID NO: 74 | TCCTCAATCCTACAACCCCGAGCGAAGAGATTCCCTGTGTAG |
| 23S | SEQ ID NO: 75 | GGGTGATAGTCCCGTAGACGAACGTGTCTAGTCCTACTCAGG |
| 23S | SEQ ID NO: 76 | GAGAGAAAGACCGACCTCAAC |
| 23S | SEQ ID NO: 77 | AGAGATTCCCTGTGTAGCG |
| 23S | SEQ ID NO: 78 | CCTTCACAGTACTGGTTCAC |
| 23S | SEQ ID NO: 79 | CTCTCCTTTCGTCTACGGGACTAACCGAGCTGATAAGGCT |
| 23S | SEQ ID NO: 80 | AAGACCGACCTCAACACCTGATTAGCCTTGGAGAGTGGTC |
| 23S | SEQ ID NO: 81 | GTTCAACTAGGAGTCCTGATCC |
| 23S | SEQ ID NO: 82 | GTAGGACTAGACACGTGAAACC |
| 23S | SEQ ID NO: 83 | CATGCTGAATACATAGGTATGC |
| 23S | SEQ ID NO: 84 | TCTAGTCCTACTCAGGTGTT |
| 23S | SEQ ID NO: 85 | TCCTTTATCCTCAATCCTACAACCCATCGAAGAGATTCCCTGTG |
| 23S | SEQ ID NO: 86 | ACTCCTAGTTGAACACATCTGGAATCTTTCTCTCCTTTCGTCTAC |

TABLE 1-continued

Primer Sequences

| Target | Sequence ID | Sequence (5' to 3') |
|---|---|---|
| 23S | SEQ ID NO: 87 | TGGATGATACAGGGTGATAGTC |
| 23S | SEQ ID NO: 88 | GGGTTGTAGGATTGAGGATAAAGG |
| 23S | SEQ ID NO: 89 | GGTTCACTATCGGTCATTGACTAG |
| 23S | SEQ ID NO: 90 | TTTCTCTCCTTTCGTCTACGGGACTATCAGG ACTCCTAGTTGAACACA |
| 23S | SEQ ID NO: 91 | ACCGACCTCAACACCTGAGTAGGTTAGCCTT GGAGAGTGGTCTC |
| 23S | SEQ ID NO: 92 | CACCCTGTATCATCCATCTTTCCAG |
| 23S | SEQ ID NO: 93 | CGTGAAACCTAGTCTGAATCTGGG |
| 23S | SEQ ID NO: 94 | CGAACTGAAACATCTTAGTAAGCAG |
| 23S | SEQ ID NO: 95 | CTCCTTTCGTCTACGGGACTA |
| 23S | SEQ ID NO: 96 | ATCAGCTCGGTTTAGGCTATTCCCGAAAAGA AATCGAAGAGATTCCCTG |
| 23S | SEQ ID NO: 97 | GCTCGGGGTTGTAGGATTGAGGATACCTGTA TCATCCATCTTTCCAGAT |
| 23S | SEQ ID NO: 98 | CTTTCGCTCGCCGCTAC |
| 23S | SEQ ID NO: 99 | GGATCAGGACTCCTAGTTGAACAC |
| 23S | SEQ ID NO: 100 | CTTACAAGCGGTCGGAGA |
| 23S | SEQ ID NO: 101 | CAGGTACTAGTTCGGTCCTC |
| 23S | SEQ ID NO: 102 | CCCTTAACCTCGCCGTTTAGCCCCGTAAGGG TCAAGGTT |
| 23S | SEQ ID NO: 103 | CCGGAGCGAAAGCGAGTTTGCTCACTTGGTT TCGTGTC |
| 23S | SEQ ID NO: 104 | TCCCTGGCTCATCATGCA |
| 23S | SEQ ID NO: 105 | GAGCGAAGAGTCGTTTGGTT |

Detection of the LAMP amplified products can be achieved via a variety of methods. In a preferred embodiment, detection of product is conducted by adding a fluorescently-labeled probe to the primer mix. The term used herein "probe" refers to a single-stranded nucleic acid molecule comprising a portion or portions that are complementary, or substantially complementary, to a target sequence. In certain implementations, the fluorescently-labeled probe is a molecular beacon.

As used herein, "molecular beacon" refers to a single stranded hairpin-shaped oligonucleotide probe designed to report the presence of specific nucleic acids in a solution. A molecular beacon consists of four components; a stem, hairpin loop, end labelled fluorophore and opposite end-labelled quencher (Tyagi et al., (1998) Nature Biotechnology 16:49-53). When the hairpin-like beacon is not bound to a target, the fluorophore and quencher lie close together and fluorescence is suppressed. In the presence of a complementary target nucleotide sequence, the stem of the beacon opens to hybridize to the target. This separates the fluorophore and quencher, allowing the fluorophore to fluoresce. Alternatively, molecular beacons also include fluorophores that emit in the proximity of an end-labelled donor. "Wavelength-shifting Molecular Beacons" incorporate an additional harvester fluorophore enabling the fluorophore to emit more strongly. Current reviews of molecular beacons include Wang et al., 2009, *Angew Chem Int Ed Engl*, 48(5):856-870; Cissell et al., 2009, *Anal Bioanal Chem* 393(1):125-35; Li et al., 2008, *Biochem Biophys Res Comm* 373(4):457-61; and Cady, 2009, *Methods Mol Biol* 554:367-79.

The term "label" as used herein means a molecule or moiety having a property or characteristic which is capable of detection and, optionally, of quantitation. A label can be directly detectable, as with, for example (and without limitation), radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, quenching moieties, light, and the like to enable detection and/or quantitation of the label. When indirectly detectable labels are used, they are typically used in combination with a "conjugate". A conjugate is typically a specific binding member that has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

The molecular beacon can be composed of nucleic acid only such as DNA or RNA, or it can be composed of a peptide nucleic acid (PNA) conjugate. The fluorophore can be any fluorescent organic dye or a single quantum dot. The quenching moiety desirably quenches the luminescence of the fluorophore. Any suitable quenching moiety that quenches the luminescence of the fluorophore can be used. A fluorophore can be any fluorescent marker/dye known in the art. Examples of suitable fluorescent markers include, but are not limited to, Fam, Hex, Tet, Joe, Rox, Tamra, Max, Edans, Cy dyes such as Cy5, Fluorescein, Coumarin, Eosine, Rhodamine, Bodipy, Alexa, Cascade Blue, Yakima Yellow, Lucifer Yellow, Texas Red, and the family of ATTO dyes. A quencher can be any quencher known in the art. Examples of quenchers include, but are not limited to, Dabcyl, Dark Quencher, Eclipse Dark Quencher, ElleQuencher, Tamra, BHQ and QSY (all of them are Trade-Marks). The skilled person would know which combinations of dye/quencher are suitable when designing a probe. In an exemplary embodiment, fluorescein (FAM) is used in conjunction with Blackhole Quencher™ (BHQ™) (Novato, Calif.). Binding of the molecular beacon to amplified product can then be directly, visually assessed. Alternatively, the fluorescence level can be measured by spectroscopy in order to improve sensitivity.

A variety of commercial suppliers produce standard and custom molecular beacons, including Abingdon Health (UK; abingdonhealth.com), Attostar (US, MN; attostar.com), Biolegio (NLD; biolegio.com), Biomers.net (DEU; biomers.net), Biosearch Technologies (US, CA; biosearchtech.com), Eurogentec (BEL; eurogentec.com), Gene Link (US, NY; genelink.com) Integrated DNA Technologies (US, IA; idtdna.com), Isogen Life Science (NLD; isogen-lifescience.com), Midland Certified Reagent (US, TX; oligos.com), Eurofins (DEU; eurofinsgenomics.eu), Sigma-Aldrich (US, TX; sigmaaldrich.com), Thermo Scientific (US, MA; thermoscientific.com), TIB MOLBIOL (DEU; tib-molbiol.de), TriLink Bio Technologies (US, CA; trilinkbiotech.com). A variety of kits, which utilize molecular beacons are also commercially available, such as the Sentinel™ Molecular Beacon Allelic Discrimination Kits from Stratagene (La Jolla, Calif.) and various kits from Eurogentec SA (Belgium, eurogentec.com) and Isogen Bioscience BV (The Netherlands, isogen.com).

The oligonucleotide probes and primers of the invention are optionally prepared using essentially any technique known in the art. In certain embodiments, for example, the oligonucleotide probes and primers described herein are synthesized chemically using essentially any nucleic acid synthesis method, including, e.g., according to the solid phase phosphoramidite triester method described by Beaucage and Caruthers (1981), Tetrahedron Setts. 22(20): 1859-1862, which is incorporated by reference, or another synthesis technique known in the art, e.g., using an automated synthesizer, as described in Needham-VanDevanter et al. (1984) Nucleic Acids Res. 12:6159-6168, which is incorporated by reference. A wide variety of equipment is commercially available for automated oligonucleotide synthesis. Multi-nucleotide synthesis approaches (e.g., tri-nucleotide synthesis, etc.) are also optionally utilized. Moreover, the primer nucleic acids described herein optionally include various modifications. To further illustrate, primers are also optionally modified to improve the specificity of amplification reactions as described in, e.g., U.S. Pat. No. 6,001,611, issued Dec. 14, 1999, which is incorporated by reference. Primers and probes can also be synthesized with various other modifications as described herein or as otherwise known in the art.

In addition, essentially any nucleic acid (and virtually any labeled nucleic acid, whether standard or non-standard) can be custom or standard ordered from any of a variety of commercial sources, such as Integrated DNA Technologies, the Midland Certified Reagent Company, Eurofins, Biosearch Technologies, Sigma Aldrich and many others.

Test samples are generally derived or isolated from subjects, typically mammalian subjects, more typically human subjects, suspected of having a *Chlamydia* infection. Exemplary samples or specimens include blood, plasma, serum, urine, synovial fluid, seminal fluid, seminal plasma, prostatic fluid, vaginal fluid, cervical fluid, uterine fluid, cervical scrapings, amniotic fluid, anal scrapings, mucus, sputum, tissue, and the like. Essentially any technique for acquiring these samples is optionally utilized including, e.g., scraping, venipuncture, swabbing, biopsy, or other techniques known in the art.

The term "test sample" as used herein, means a sample taken from an organism or biological fluid that is suspected of containing or potentially contains a target sequence. The test sample can be taken from any biological source, such as for example, tissue, blood, saliva, sputa, mucus, sweat, urine, urethral swabs, cervical swabs, vaginal swabs, urogenital or anal swabs, conjunctival swabs, ocular lens fluid, cerebral spinal fluid, milk, ascites fluid, synovial fluid, peritoneal fluid, amniotic fluid, fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma or serum from blood, disrupting cells or viral particles, preparing liquids from solid materials, diluting viscous fluids, filtering liquids, distilling liquids, concentrating liquids, inactivating interfering components, adding reagents, purifying nucleic acids, and the like.

Advantageously, the invention enables reliable rapid detection of *Chlamydia trachomatis* in a clinical sample, such as a urine sample.

To further illustrate, prior to analyzing the target nucleic acids described herein, those nucleic acids may be purified or isolated from samples that typically include complex mixtures of different components. Cells in collected samples are typically lysed to release the cell contents. For example, *C. trachomatis* and other cells in the particular sample can be lysed by contacting them with various enzymes, chemicals, and/or lysed by other approaches known in the art, which degrade, e.g., bacterial cell walls. In some embodiments, nucleic acids are analyzed directly in the cell lysate. In other embodiments, nucleic acids are further purified or extracted from cell lysates prior to detection. Essentially any nucleic acid extraction methods can be used to purify nucleic acids in the samples utilized in the methods of the present invention. Exemplary techniques that can be used to purifying nucleic acids include, e.g., affinity chromatography, hybridization to probes immobilized on solid supports, liquid-liquid extraction (e.g., phenol-chloroform extraction, etc.), precipitation (e.g., using ethanol, etc.), extraction with filter paper, extraction with micelle-forming reagents (e.g., cetyl-trimethyl-ammonium-bromide, etc.), binding to immobilized intercalating dyes (e.g., ethidium bromide, acridine, etc.), adsorption to silica gel or diatomic earths, adsorption to magnetic glass particles or organo silane particles under chaotropic conditions, and/or the like. Sample processing is also described in, e.g., U.S. Pat. Nos. 5,155,018, 6,383,393, and 5,234,809, which are each incorporated by reference.

A test sample may optionally have been treated and/or purified according to any technique known by the skilled person, to improve the amplification efficiency and/or qualitative accuracy and/or quantitative accuracy. The sample may thus exclusively, or essentially, consist of nucleic acid(s), whether obtained by purification, isolation, or by chemical synthesis. Means are available to the skilled person, who would like to isolate or purify nucleic acids, such as DNA, from a test sample, for example to isolate or purify DNA from cervical scrapes (e.g., QIAamp-DNA Mini-Kit; Qiagen, Hilden, Germany).

EXAMPLES

Example 1

Target Selection and Primer Probe Design

Considering the constitutive and high level of expression of the ribosomal genes in bacterial cells, these genes were chosen as targets for the amplification assay, specifically the 16S and 23S genes.

16S and 23S gene sequences for multiple serovars of *C. trachomatis*, closely related species such as *Chlamydophila pneumoniae* and *Chlamydia psittaci*, and for other species commonly found in the urine or vaginal fluid were retrieved from the NCBI database. Sequences were aligned using Clustal omega (Sievers, et al. 2011. Molecular Systems Biology 7:539) and regions with unique specific bases to *C. trachomatis* species were identified. Loop mediated amplification primers were designed using LAMP designer (Premier Biosoft). For added specificity, molecular beacons or probes targeting the amplified products were designed manually or using Beacon designer (Premier Biosoft).

Designed primer sets and beacons were further analyzed for specificity using BLAST against the human genome and the NCBI nucleotide database. Various primer sets and probes were designed and screened for reaction speed.

The inventive primer sets are summarized in Table 2, which include, at a minimum, a forward inner primer (FIP) and backward inner primer (BIP). Additionally, the primer sets typically also include at least two additional primers selected from the forward outer primer (F3), backward outer primer (B3), forward loop primer (LF) and backward loop primer (LB).

TABLE 2

LAMP Primer Sets

| Set | F3 | B3 | FIP | BIP | LF | LB |
|---|---|---|---|---|---|---|
| Set-1 | SEQ ID NO: 1 | SEQ ID NO: 2 | SEQ ID NO: 3 | SEQ ID NO: 4 | SEQ ID NO: 5 | SEQ ID NO: 6 |
| Set-2 | SEQ ID NO: 1 | SEQ ID NO: 2 | SEQ ID NO: 7 | SEQ ID NO: 4 | SEQ ID NO: 8 | SEQ ID NO: 6 |
| Set-3 | SEQ ID NO: 9 | SEQ ID NO: 10 | SEQ ID NO: 11 | SEQ ID NO: 12 | SEQ ID NO: 8 | SEQ ID NO: 13 |
| Set-4 | SEQ ID NO: 14 | SEQ ID NO: 15 | SEQ ID NO: 16 | SEQ ID NO: 17 | SEQ ID NO: 5 | SEQ ID NO: 18 |
| Set-5 | SEQ ID NO: 19 | SEQ ID NO: 20 | SEQ ID NO: 21 | SEQ ID NO: 22 | SEQ ID NO: 23 | SEQ ID NO: 24 |
| Set-6 | SEQ ID NO: 25 | SEQ ID NO: 26 | SEQ ID NO: 27 | SEQ ID NO: 22 | SEQ ID NO: 29 | SEQ ID NO: 30 |
| Set-7 | SEQ ID NO: 31 | SEQ ID NO: 32 | SEQ ID NO: 33 | SEQ ID NO: 34 | SEQ ID NO: 35 | SEQ ID NO: 36 |
| Set-8 | SEQ ID NO: 37 | SEQ ID NO: 38 | SEQ ID NO: 39 | SEQ ID NO: 40 | SEQ ID NO: 41 | SEQ ID NO: 42 |
| Set-9 | SEQ ID NO: 43 | SEQ ID NO: 44 | SEQ ID NO: 45 | SEQ ID NO: 46 | SEQ ID NO: 47 | SEQ ID NO: 48 |
| Set-10 | — | — | SEQ ID NO: 3 | SEQ ID NO: 4 | SEQ ID NO: 5 | SEQ ID NO: 6 |
| Set-11 | — | — | SEQ ID NO: 3 | SEQ ID NO: 4 | — | — |
| Set-12 | — | — | SEQ ID NO: 7 | SEQ ID NO: 4 | SEQ ID NO: 8 | SEQ ID NO: 6 |
| Set-13 | — | — | SEQ ID NO: 11 | SEQ ID NO: 12 | SEQ ID NO: 8 | SEQ ID NO: 13 |
| Set-14 | — | — | SEQ ID NO: 16 | SEQ ID NO: 17 | SEQ ID NO: 5 | SEQ ID NO: 18 |
| Set-15 | — | — | SEQ ID NO: 21 | SEQ ID NO: 22 | SEQ ID NO: 23 | SEQ ID NO: 24 |
| Set-16 | — | — | SEQ ID NO: 27 | SEQ ID NO: 28 | SEQ ID NO: 29 | SEQ ID NO: 30 |
| Set-17 | — | — | SEQ ID NO: 33 | SEQ ID NO: 34 | SEQ ID NO: 35 | SEQ ID NO: 36 |
| Set-18 | — | — | SEQ ID NO: 39 | SEQ ID NO: 40 | SEQ ID NO: 41 | SEQ ID NO: 42 |
| Set-19 | — | — | SEQ ID NO: 45 | SEQ ID NO: 46 | SEQ ID NO: 47 | SEQ ID NO: 48 |
| Set-20 | SEQ ID NO: 1 | SEQ ID NO: 2 | SEQ ID NO: 3 | SEQ ID NO: 4 | — | — |
| Set-21 | SEQ ID NO: 1 | SEQ ID NO: 2 | SEQ ID NO: 7 | SEQ ID NO: 4 | — | — |
| Set-22 | SEQ ID NO: 9 | SEQ ID NO: 10 | SEQ ID NO: 11 | SEQ ID NO: 12 | — | — |
| Set-23 | SEQ ID NO: 14 | SEQ ID NO: 15 | SEQ ID NO: 16 | SEQ ID NO: 17 | — | — |
| Set-24 | SEQ ID NO: 19 | SEQ ID NO: 20 | SEQ ID NO: 21 | SEQ ID NO: 22 | — | — |
| Set-25 | SEQ ID NO: 25 | SEQ ID NO: 26 | SEQ ID NO: 27 | SEQ ID NO: 28 | — | — |
| Set-26 | SEQ ID NO: 31 | SEQ ID NO: 32 | SEQ ID NO: 33 | SEQ ID NO: 34 | — | — |
| Set-27 | SEQ ID NO: 37 | SEQ ID NO: 38 | SEQ ID NO: 39 | SEQ ID NO: 40 | — | — |
| Set-28 | SEQ ID NO: 43 | SEQ ID NO: 44 | SEQ ID NO: 45 | SEQ ID NO: 46 | — | — |
| Set-29 | — | — | SEQ ID NO: 7 | SEQ ID NO: 4 | — | — |
| Set-30 | — | — | SEQ ID NO: 11 | SEQ ID NO: 12 | — | — |
| Set-31 | — | — | SEQ ID NO: 16 | SEQ ID NO: 17 | — | — |
| Set-32 | — | — | SEQ ID NO: 21 | SEQ ID NO: 22 | — | — |
| Set-33 | — | — | SEQ ID NO: 27 | SEQ ID NO: 28 | — | — |
| Set-34 | — | — | SEQ ID NO: 33 | SEQ ID NO: 34 | — | — |
| Set-35 | — | — | SEQ ID NO: 39 | SEQ ID NO: 40 | — | — |
| Set-36 | — | — | SEQ ID NO: 45 | SEQ ID NO: 46 | — | — |
| Set-37 | SEQ ID NO: 60 | SEQ ID NO: 61 | SEQ ID NO: 62 | SEQ ID NO: 63 | SEQ ID NO: 64 | SEQ ID NO: 65 |
| Set-38 | SEQ ID NO: 66 | SEQ ID NO: 67 | SEQ ID NO: 68 | SEQ ID NO: 69 | SEQ ID NO: 70 | SEQ ID NO: 71 |
| Set-39 | SEQ ID NO: 72 | SEQ ID NO: 73 | SEQ ID NO: 74 | SEQ ID NO: 75 | SEQ ID NO: 5 | SEQ ID NO: 76 |
| Set-40 | SEQ ID NO: 77 | SEQ ID NO: 78 | SEQ ID NO: 79 | SEQ ID NO: 80 | SEQ ID NO: 81 | SEQ ID NO: 82 |
| Set-41 | SEQ ID NO: 83 | SEQ ID NO: 84 | SEQ ID NO: 85 | SEQ ID NO: 86 | SEQ ID NO: 8 | SEQ ID NO: 87 |
| Set-42 | SEQ ID NO: 88 | SEQ ID NO: 89 | SEQ ID NO: 90 | SEQ ID NO: 91 | SEQ ID NO: 92 | SEQ ID NO: 93 |
| Set-43 | SEQ ID NO: 94 | SEQ ID NO: 95 | SEQ ID NO: 96 | SEQ ID NO: 97 | SEQ ID NO: 98 | SEQ ID NO: 99 |
| Set-44 | SEQ ID NO: 100 | SEQ ID NO: 101 | SEQ ID NO: 102 | SEQ ID NO: 103 | SEQ ID NO: 104 | SEQ ID NO: 105 |
| Set-45 | — | — | SEQ ID NO: 62 | SEQ ID NO: 63 | SEQ ID NO: 64 | SEQ ID NO: 65 |
| Set-46 | — | — | SEQ ID NO: 68 | SEQ ID NO: 69 | SEQ ID NO: 70 | SEQ ID NO: 71 |
| Set-47 | — | — | SEQ ID NO: 74 | SEQ ID NO: 75 | SEQ ID NO: 5 | SEQ ID NO: 76 |
| Set-48 | — | — | SEQ ID NO: 79 | SEQ ID NO: 80 | SEQ ID NO: 81 | SEQ ID NO: 82 |
| Set-49 | — | — | SEQ ID NO: 85 | SEQ ID NO: 86 | SEQ ID NO: 8 | SEQ ID NO: 87 |
| Set-50 | — | — | SEQ ID NO: 96 | SEQ ID NO: 97 | SEQ ID NO: 98 | SEQ ID NO: 99 |
| Set-51 | — | — | SEQ ID NO: 102 | SEQ ID NO: 103 | SEQ ID NO: 104 | SEQ ID NO: 105 |
| Set-52 | SEQ ID NO: 60 | SEQ ID NO: 61 | SEQ ID NO: 62 | SEQ ID NO: 63 | — | — |
| Set-53 | SEQ ID NO: 66 | SEQ ID NO: 67 | SEQ ID NO: 68 | SEQ ID NO: 69 | — | — |
| Set-54 | SEQ ID NO: 72 | SEQ ID NO: 73 | SEQ ID NO: 74 | SEQ ID NO: 75 | — | — |
| Set-55 | SEQ ID NO: 77 | SEQ ID NO: 78 | SEQ ID NO: 79 | SEQ ID NO: 80 | — | — |
| Set-56 | SEQ ID NO: 83 | SEQ ID NO: 84 | SEQ ID NO: 85 | SEQ ID NO: 86 | — | — |
| Set-57 | SEQ ID NO: 94 | SEQ ID NO: 95 | SEQ ID NO: 96 | SEQ ID NO: 97 | — | — |
| Set-58 | SEQ ID NO: 100 | SEQ ID NO: 101 | SEQ ID NO: 102 | SEQ ID NO: 103 | — | — |

Example 2

Amplification Reaction Kinetics

A negative urine matrix was spiked with titred *C. trachomatis* (serially diluted in PBS, Zeptometrix CN #0801775) at two different concentrations ($10^3$ IFU/mL and 10 IFU/mL). Nucleic acids were extracted using standard extraction methods and the sample was amplified using LAMP primers (SEQ ID NOs: 1-6). YoPro™ dye (Life Technologies; green fluorescent carbocyanine nucleic acid stain) was used for the detection of the amplified product. In this example a 25 µl reaction contained 1× Isothermal Amplification Buffer (New England Biolabs) supplemented with 4.8 mM or 6 mM $MgCl_2$, 1.4 mM or 1.6 mM dNTP, 200 nM YO-PRO-1 dye (Life Technologies), primers (2 µM of F3 and B3, when present; 1.6 µM of FIP and BIP; 8 µM of LF and LB, when present), 8 or 12 Units of Bst2 polymerase (New England Biolabs), 7.5 Units RTx Warmstart (reverse transcriptase; New England Biolabs), and the extracted nucleic acid (as template) or water (as no template control). The reactions were incubated at 63° or 65° C. and kinetics were monitored using a Roche real-time Lightcycler96 (Roche).

This example shows that using this set of primers and the loop mediated amplification method, fast amplification kinetics are achieved. Results are summarized in Table 3, in which the Time to Positive (Tp) was calculated by the instrument. Results are classified by the time to position: A having Tp in less or equal to 8 minutes, B having Tp between 8 minutes and 12 minutes (inclusive), and C having Tp greater than 12 minutes.

TABLE 3

Time to Positive Dye Detection

| primers | $T_p$ $10^3$ IFU/mL | $T_p$ 10 IFU/mL |
|---|---|---|
| Set-1 | A | A |
| Set-2 | A | B |
| Set-3 | A | A |
| Set-4 | B | C |
| Set-5 | A | B |
| Set-6 | A | A |
| Set-7 | C | C |

Example 3

Beacon Design Location Effect on Assay Kinetics

Amplification reactions containing some of the above primers sets and the intercalating dye resulted in the detection of an amplification product when using water or negative urine extraction or the DNA of closely related specie such as *C. pneumoniae* or *C. psittaci* as templates at frequencies ranging between 0% to 75% of the time (Table 4), within variable intervals of our cut off window for the assay time. Results are classified by the time to position: A having Tp in less or equal to 8 minutes, B having Tp between 8 minutes and 12 minutes (inclusive), C having Tp greater than 12 minutes, and D having no amplification detected.

TABLE 4

Cross Reactivity—Dye Detection

| Set | Negative Urine extraction | | NTC (water) | | *C. pneumoniae* DNA | | *C. psittaci* DNA | |
|---|---|---|---|---|---|---|---|---|
| Set-1 | C | 2 of 4 | C | 1 of 2 | C | 2 of 2 | C | 2 of 2 |
| Set-2 | D | 0 of 4 | D | 0 of 2 | C | 1 of 2 | D | 0 of 2 |
| Set-3 | D | 0 of 4 | B | 1 of 2 | C | 1 of 2 | C | 2 of 2 |
| Set-4 | C | 1 of 4 | D | 0 of 2 | D | 0 of 2 | C | 1 of 2 |
| Set-5 | C | 1 of 4 | D | 0 of 2 | D | 0 of 2 | C | 1 of 2 |
| Set-6 | C | 3 of 4 | C | 1 of 2 | C | 2 of 2 | C | 1 of 2 |

For added specificity molecular beacons were designed along these primers sets to make sure only signal from the *C. trachomatis* target is detected (sequences listed in table 5). Each molecular beacon probe was designed with 5' fluorophore/3' quencher modifications (6-Carboxyfluorescein (FAM) and Black Hole Quencher 1 (BHQ1)) included to provide target-specific fluorescent detection.

TABLE 5

Probe Sequences

| ID | Fluor | Quench | Sequence (5' to 3') | Sequence ID |
|---|---|---|---|---|
| MB1 | FAM | BHQ1 | CGCGATCAGGACTCCTAGTTGAA CACATCTGGATCGCG | SEQ ID NO: 49 |
| MB2 | FAM | BHQ1 | CGTCCAGGACTCCTAGTTGAACA CATCTGGACG | SEQ ID NO: 50 |
| MB3 | FAM | BHQ1 | CGCGACTCAGGACTCCTAGTTGA ACACATCTGGAGTCGCG | SEQ ID NO: 51 |
| MB4 | FAM | BHQ1 | CGCGAGTAGGATTGAGGATAAAG GATCAGGACTCGCG | SEQ ID NO: 52 |
| MB5 | FAM | BHQ1 | CGCGCACATCTGGAAAGATGGAT GATACAGGGTGCGCG | SEQ ID NO: 53 |
| MB6 | FAM | BHQ1 | CGCGATCCGGATAAAGGATCAGG ACTCCTA GTTG GGATCGCG | SEQ ID NO: 54 |
| MB7 | FAM | BHQ1 | CGCGATCAGACCGACCTCAACAC CTGAGATCGCG | SEQ ID NO: 55 |
| MB8 | FAM | BHQ1 | CGCAGTGAGAGAAAGACCGACCT CAACACTGCG | SEQ ID NO: 56 |
| MB9 | FAM | BHQ1 | CGCGATC CTGTGTAGCGGCGAG CGAAA GATCGCG | SEQ ID NO: 57 |
| MB10 | FAM | BHQ1 | CGCGATC ATCCGAGTAACGTTA AAGAAGGGATCGCG | SEQ ID NO: 58 |
| MB11 | FAM | BHQ1 | CGCGATCTGGCGATATTTGGGCA TCCGAGATCGCG | SEQ ID NO: 59 |
| MB12 | FAM | BHQ1 | CGCGATCAGATCCATGGCATAAG TAACGGATCGCG | SEQ ID NO: 106 |
| MB13 | FAM | BHQ1 | CGCGATCGGTGAAGATCCATGGC ATAAGTAACGCGATCGCG | SEQ ID NO: 107 |
| MB14 | FAM | BHQ1 | CGCGATCCATGGCATAAGTAACG ATAAAGGGAGTGAGGATCGCG | SEQ ID NO: 108 |
| MB15 | FAM | BHQ1 | CGCGATCATGACGGAGTAAGTTA AGCACGCGATCGCG | SEQ ID NO: 109 |
| MB16 | FAM | BHQ1 | CGCGATGTCTGGAAAGATGGATG ATACAGCATCGCG | SEQ ID NO: 110 |
| MB17 | FAM | BHQ1 | CGCGATCTGAGGATAAAGGATCA GGACTCGATCGCG | SEQ ID NO: 111 |

TABLE 5-continued

Probe Sequences

| ID | Fluor | Quench | Sequence (5' to 3') | Sequence ID |
|---|---|---|---|---|
| MB18 | FAM | BHQ1 | CGCGATCCCTGTGTAGCGGCGAG CGAGATCGCG | SEQ ID NO: 112 |
| MB19 | FAM | BHQ1 | CGCGATCGCAAAAGGCACGCCGT CAAGATCGCG | SEQ ID NO: 113 |
| MB20 | FAM | BHQ1 | CGGCTCGGGGTTGTAGGATTGAG GATACGAGCCG | SEQ ID NO: 114 |
| MB21 | FAM | BHQ1 | CCGGAGCCTACAACCCCGAGCCT TATCAGCTCCGG | SEQ ID NO: 115 |
| MB22 | FAM | BHQ1 | CGCGCAGCTCGGTTTAGGCTATT CCCCTGCGCG | SEQ ID NO: 116 |
| MB23 | FAM | BHQ1 | CGCGGTCTCTCCTTTCGTCTACG GGACCGCG | SEQ ID NO: 117 |

A negative urine matrix was spiked with titred *C. trachomatis* (serially diluted in PBS, Zeptometrix CN #0801775) at two different concentrations ($10^3$ IFU/mL and 10 IFU/mL). Nucleic acids were extracted using standard extraction methods and the sample was amplified using a LAMP primer set (Sets described in Table 2, SEQ ID NOs) and one of the molecular beacons (table 4) was used for the detection of the amplified product. In this example a 25 µl reaction contained 1× Isothermal Amplification Buffer or Thermopol DF buffer (New England Biolabs) supplemented with 4.8 mM or 6 mM MgCl$_2$, 1.4 mM or 1.6 mM dNTP, 200 nM molecular beacon (Sigma-Aldrich), primers (0.2 µM of F3 and B3, if present; 1.6 µM or 2 µM of FIP and BIP; 8 µM of LF and LB, if present), 8 or 12 Units of Bst2 polymerase (New England Biolabs), 7.5 Units RTx Warmstart (reverse transcriptase; New England Biolabs), and the extracted nucleic acid (as template) or water (as no template control). The reactions were incubated at 63° C. or 65° C. and kinetics were monitored using a Roche real-time Lightcycler96 (Roche). The time to positive for each primer-probe combination is reported in Table 6. Results are classified by the time to positive (Tp) from reaction initiation as follows: "A" indicates a Tp of less than or equal to 10 minutes, "B" indicates a Tp of between 10 minutes and 15 minutes (inclusive), and "C" indicates a Tp of greater than 15 minutes. "NT" indicates that this combination was not tested.

TABLE 6

Time to Positive Probe Detection

| Primers | Beacon | $10^3$ IFU/mL | 10 IFU/mL |
|---|---|---|---|
| Set-1 | MB1 | A | A |
| Set-1 | MB1 | A | B |
| Set-1 | MB3 | B | C |
| Set-1 | MB4 | A | B |
| Set-1 | MB5 | B | B |
| Set-1 | MB9 | C | C |
| Set-2 | MB1 | B | B |
| Set-3 | MB5 | B | B |
| Set-3 | MB1 | A | B |
| Set-4 | MB6 | C | C |
| Set-5 | MB7 | A | B |
| Set-6 | MB8 | B | B |
| Set-7 | MB10 | B | C |
| Set-8 | MB10 | B | C |
| Set-9 | MB11 | B | NT |
| Set-37 | MB12 | B | NT |
| Set-37 | MB13 | C | C |

TABLE 6-continued

Time to Positive Probe Detection

| Primers | Beacon | $10^3$ IFU/mL | 10 IFU/mL |
|---|---|---|---|
| Set-37 | MB14 | A | B |
| Set-38 | MB15 | B | NT |
| Set-39 | MB1 | NT | C |
| Set-40 | MB1 | C | C |
| Set-1 | MB1 | A | B |
| Set-1 | MB16 | B | C |
| Set-1 | MB17 | B | C |
| Set-1 | MB18 | A | A |
| Set-1 | MB9 | B | C |
| Set-41 | MB1 | A | A |
| Set-42 | MB8 | A | B |
| Set-42 | MB7 | A | NT |
| Set-43 | MB2 | A | A |
| Set-3 | MB18 | B | B |
| Set-3 | MB1 | A | B |
| Set-4 | MB1 | B | C |
| Set-43 | MB20 | A | B |

*Chlamydia trachomatis* gDNA (ATCC CN #VR-885D) was diluted using TE buffer at two different concentrations ($10^5$ genome copies/µl and $10^3$ genome copies/µl). The sample was amplified using a LAMP primer set (Sets described in Table 2, SEQ ID NOs) and one of the molecular beacons (Table 5) was used for the detection of the amplified product. In this example a 25 µl reaction contained 1× Isothermal Amplification Buffer or Thermopol DF buffer (New England Biolabs) supplemented with 4.8 mM or 6 mM MgCl$_2$, 1.4 mM or 1.6 mM dNTP, 200 nM molecular beacon(Sigma-Aldrich), primers (0.2 µM of F3 and B3, if present; 1.6 µM or 2 µM of FIP and BIP; 0.8 µM of LF and LB, if present), 8 or 12 Units of Bst2 polymerase (New England Biolabs), 7.5 Units RTx Warmstart (reverse transcriptase; New England Biolabs), and the gDNA dilutions (as template) or water (as no template control). The reactions were incubated at 63° C. or 65° C. and kinetics were monitored using a Roche real-time Lightcycler96 (Roche). The time to positive for each primer-probe combination is reported in Table 7. Results are classified by the time to positive: A having Tp in less or equal to 10 minutes, B having Tp between 10 minutes and 15 minutes (inclusive), C having Tp greater that 15 minutes. NT indicates that this combination was not tested.

TABLE 7

Time to Positive Probe Detection

| Primers | Beacon | $5 \times 10^5$ genome copies/reaction | $5 \times 10^3$ genome copies/reaction |
|---|---|---|---|
| Set-1 | MB21 | A | A |
| Set-1 | MB22 | A | A |
| Set-1 | MB23 | A | A |

Use of Molecular Beacons for detection resulted in a slight increase in reaction Tp, however the significant enhancement in assay specificity provided a reasonable tradeoff, no amplification was observed in the negative urine extract or water sample or DNA from a close related species within the testing period of 45 min.

Example 4

Specificity Testing

A negative urine matrix was spiked with titred *C. trachomatis* or with organisms commonly associated with urine infections at high loads (e.g., *E. coli, C. albicans, S. aureus*, P. mirabilis), sexually transmitted infections (e.g., Neisseria gonorrhoeae) or species closely related to C. trachomatis (C. pneumonia or C. psittaci). Bacterial stocks were serially diluted in PBS before addition to the urine matrix at the desired concentration. Corresponding extracted nucleic acids or DNAs of the test species were used as templates in RT-LAMP reactions containing the LAMP primers (set-1) and the molecular beacon probe MB2. Reaction conditions are equivalent to those described above in Example 3. The designed primers and probe resulted in no amplification after 45 minutes with the non-C. trachomatis species tested.

This example shows that the designed CT23S assay and its reaction formulation is highly specific and does not cross react with sequences of organisms commonly found in urine and vaginal clinical samples.

Example 5

Sensitivity Testing

A negative urine matrix was spiked with titred C. trachomatis at various concentrations ($10^4$ IFU/mL to 1 IFU/mL). Bacterial stock was serially diluted in PBS before addition to the urine matrix at the desired concentration. Extracted samples were amplified using LAMP primers (Table 2) and the molecular beacon probe (Table 5). Reaction conditions were equivalent to those described above in Example 3. Amplification signal was obtained with concentrations as low as 0.05 IFU/reaction (see Table 8). Results are classified by the time to positive (Tp) from reaction initiation as follows: "A" indicates a Tp of less than or equal to 10 minutes, "B" indicates a Tp of between 10 minutes and 15 minutes (inclusive), and "C" indicates a Tp of greater than 15 minutes. "NT" indicates that this combination was not tested.

TABLE 8

Sensitivity testing with different primer sets and corresponding beacons

| Set | MB | $10^3$ IFU/mL | 100 IFU/mL | 10 IFU/mL | 4 IFU/mL | 2 IFU/mL |
|---|---|---|---|---|---|---|
| Set-1 | MB1 | A | A | A | B | B |
| Set-1 | MB2 | NT | NT | A | B | B |
| Set-3 | MB1 | A | A | B | NT | C |
| Set-9 | MB11 | B | NT | NT | C | C |

Example 6

Limit of Detection Estimation

A negative urine matrix was spiked with titred C. trachomatis at various concentrations (10 IFU/mL, 4 IFU/mL, 2 IFU/mL). Similarly, swabs (BD BBL culture Swab EZ Collection and Transport System single swab Fisher Cat #220144) were infused with C. trachomatis diluted to the same concentrations as used in the urine. Bacterial stock was serially diluted in PBS before addition to the urine matrix or infused to the swab at the desired concentration. For each experiment (for each bacterial serial dilution), one nucleic acid extraction was performed from C. trachomatis in urine or on a swab at 10 IFU/mL, 10 extractions from samples at 4 IFU/mL, 10 extractions from samples at 2 IFU/mL and one extraction from negative urine or swab matrix. The experiment was repeated 3 times on different days by different operators. One tenth of each extracted sample was amplified using the LAMP primers (Set-1) and the molecular beacon probe MB2 listed in Table 5. In this example the 25 µl reaction contained the Isothermal buffer 1× (New England Biolabs) supplemented with 4.8 mM MgCl2, 1.6 mM dNTP, 200 nM of molecular beacon (Sigma Aldrich), primers (0.2 µM of F3 and B3; 2 µM of FIP and BIP; 0.8 µM of LF and LB), 12 Units of Bst2 polymerase (New England Biolabs), 7.5 Units RTx Warmstart (New England Biolabs), and nucleic acid template or water (as no template control). The reactions were incubated at 63° C. and kinetics were monitored using the Roche real-time Lightcycler96 (Roche). Two RT-LAMP reactions were run per extraction. Reactions were scored positive if their Cq were below 15 cycles. The frequency detection of C. trachomatis in urine or swab was calculated based on the number of positive reactions divided by the total number of reactions (Table 9). All reactions originating from samples at 10 IFU/mL were positives, those originating from negative swab or urine samples were negative. The limit of detection for this assay is estimated to be around 4 IFU/mL for both urine and swab samples. Bacterial load is the concentration in the starting material (urine or swab) 0.5 mL is used for the extractions. Detection was determined to be positive if Tp was less than 15 minutes.

TABLE 9

Limit of Detection

| Specimen Type | Bacterial Load [b] | Number of wells detected [c] | % detected |
|---|---|---|---|
| Urine | 4 IFU/mL | 64/68 | 94.1 |
|  | 2 IFU/mL | 35/60 | 58.3 |
| Swab | 4 IFU/mL | 60/64 | 93.7 |
|  | 2 IFU/mL | 39/60 | 65 |

Example 7

Limited Primer Sets

To assess the contribution of each primer set to the RTLAMP reaction, we also investigated use of just the inner primers or the inner primers plus the loop primers and compared those reactions to the complete 6 primer RTLAMP reaction, using a Molecular Beacon for detection. Table 10 provides an example using an assay comprised of various subsets of Set-1 and MB1. Interestingly and noteworthy, the reaction still proceeds when the F3/B3 primers (Set-10) are excluded. The absence of F3/B3 appears to have an impact on sensitivity, specifically consistency at low concentrations (Table 10, indicated IFU is per mL of sample, 0.5 mL are used for the extraction, 5 uL of which was used per RTLAMP reaction). The reaction does proceed if only the inner primers are included (Set-11) with substantial delays in the onset of reaction at the highest concentration tested and the sensitivity being poor. Results are classified by the time to positive (Tp) from reaction initiation as follows: "A" indicates a Tp of less than or equal to 10 minutes, "B" indicates a Tp of between 10 minutes and 15 minutes (inclusive), and "C" indicates a Tp of greater than 15 minutes. "ND" indicates that no amplification was detected.

TABLE 10

Contribution of Primer Pairs

| Primer Combination | Assay Tp | | | |
|---|---|---|---|---|
|  | 500 IFU | 10 IFU/mL | 2 IFU/ml | NTC |
| Set-1 | A | B | B | ND |
| Set-10 | A | B | C | ND |
| Set-11 | C | ND | ND | ND |

We claim:

1. A method of detecting *Chlamydia trachomatis* in a test sample, the method comprising:
    (a) extracting nucleic acid from the test sample;
    (b) amplifying a target sequence by reacting the nucleic acid extracted in step (a) with a reaction mixture comprising a strand displacement DNA polymerase and a sequence-specific primer set comprising Set-1, wherein Set-1 comprises SEQ ID NO: 3 and SEQ ID NO: 4; and
    (c) detecting the presence or absence of an amplified product of step (b); wherein the presence of said amplification product is indicative of the presence of *Chlamydia trachomatis* in the test sample.

2. The method of claim 1, wherein the amplification in step (b) of the target sequence is performed at between about 60° C. and about 67° C. for less than 30 minutes.

3. The method of claim 1, wherein the amplification step is performed for less than 15 minutes.

4. The method of claim 3, wherein the amplification step is performed for less than nine minutes.

5. The method of claim 1, wherein detecting the presence or absence of the amplification product comprises hybridizing the amplified product with a probe comprising a polynucleotide attached to a label.

6. The method of claim 5, wherein the probe is a molecular beacon.

7. The method of claim 1, wherein the reaction mixture further comprises a reverse transcriptase.

8. The method of claim 1, wherein *Chlamydia trachomatis* is present in the test sample at a concentration of ≤100 inclusion-forming units/ml (IFU/ml).

9. The method of claim 8, wherein *Chlamydia trachomatis* is present in the test sample at a concentration of ≤50 IFU/ml.

10. The method of claim 9, wherein *Chlamydia trachomatis* is present in the test sample at a concentration of ≤5 IFU/ml.

11. The method of claim 10, wherein *Chlamydia trachomatis* is present in the test sample at a concentration of ≤2 IFU/ml and the amplification step is performed for less than 15 minutes.

* * * * *